US009683232B2

(12) United States Patent
Yamanaka et al.

(10) Patent No.: US 9,683,232 B2
(45) Date of Patent: Jun. 20, 2017

(54) EFFICIENT METHOD FOR NUCLEAR REPROGRAMMING

(75) Inventors: Shinya Yamanaka, Kyoto (JP); Michiyo Koyanagi, Kyoto (JP)

(73) Assignee: Kyoto University, Kyoto (JP)

( * ) Notice: Subject to any disclaimer, the term of this patent is extended or adjusted under 35 U.S.C. 154(b) by 697 days.

(21) Appl. No.: 12/379,564

(22) Filed: Feb. 25, 2009

(65) Prior Publication Data

US 2009/0246875 A1  Oct. 1, 2009

Related U.S. Application Data

(63) Continuation-in-part of application No. 12/292,717, filed on Nov. 25, 2008, now abandoned, which is a continuation-in-part of application No. PCT/JP2008/059586, filed on May 23, 2008.

(60) Provisional application No. 60/996,893, filed on Dec. 10, 2007.

(30) Foreign Application Priority Data

Dec. 8, 2008 (JP) .................... 2008-312745
Dec. 26, 2008 (JP) .................... 2008-335129

(51) Int. Cl.
C12N 15/64 (2006.01)
C12N 15/113 (2010.01)
C12N 5/074 (2010.01)

(52) U.S. Cl.
CPC .......... *C12N 15/113* (2013.01); *C12N 5/0696* (2013.01); *C12N 2310/141* (2013.01); *C12N 2320/30* (2013.01); *C12N 2330/10* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/65* (2013.01); *C12N 2510/00* (2013.01)

(58) Field of Classification Search
CPC ................ C12N 15/113; C12N 5/0696; C12N 2310/141; C12N 2320/30; C12N 2330/10; C12N 2501/602; C12N 2501/603; C12N 2501/604; C12N 2501/605; C12N 2501/606; C12N 2501/65; C12N 2510/00
See application file for complete search history.

(56) References Cited

U.S. PATENT DOCUMENTS

| | | |
|---|---|---|
| 7,250,255 B2 | 7/2007 | Yamanaka |
| 2003/0044976 A1 | 3/2003 | Dominko et al. |
| 2004/0137460 A1 | 7/2004 | Yamanaka et al. |
| 2005/0130144 A1 | 6/2005 | Nakatsuji et al. |
| 2006/0110830 A1 | 5/2006 | Dominko et al. |
| 2006/0292620 A1 | 12/2006 | Yamanaka et al. |
| 2007/0155013 A1 | 7/2007 | Akaike et al. |
| 2008/0003560 A1 | 1/2008 | Nakatsuji et al. |
| 2008/0076176 A1 | 3/2008 | Dominko et al. |
| 2008/0233610 A1 | 9/2008 | Thomson et al. |
| 2008/0274914 A1 | 11/2008 | Yamanaka |
| 2008/0280362 A1 | 11/2008 | Jaenisch et al. |
| 2008/0293143 A1 | 11/2008 | Lin et al. |
| 2008/0299548 A1 | 12/2008 | Yamanaka |
| 2009/0047263 A1 | 2/2009 | Yamanaka et al. |
| 2009/0068742 A1 | 3/2009 | Yamanaka |
| 2009/0191159 A1 | 7/2009 | Sakurada et al. |
| 2009/0304646 A1 | 12/2009 | Sakurada et al. |

FOREIGN PATENT DOCUMENTS

| | | |
|---|---|---|
| AU | 2008201280 A1 | 4/2008 |
| JP | 2002-065261 | 3/2002 |
| JP | 2003-009854 | 1/2003 |
| JP | 2004-161682 | 6/2004 |
| JP | 2005-095027 | 4/2005 |
| JP | 2008-283972 | 11/2008 |
| WO | 00/18885 | 4/2000 |
| WO | 00/27995 A1 | 5/2000 |
| WO | 01/34776 A1 | 5/2001 |
| WO | 01/51616 A2 | 7/2001 |
| WO | 01/81549 A2 | 11/2001 |
| WO | 02/061033 A2 | 8/2002 |
| WO | 02/097090 A1 | 12/2002 |
| WO | 03/018780 A1 | 3/2003 |
| WO | 2004/081205 A1 | 9/2004 |
| WO | 2005/080598 A1 | 9/2005 |
| WO | 2005/090557 A1 | 9/2005 |
| WO | 2006/035741 A1 | 4/2006 |
| WO | 2007/026255 A2 | 3/2007 |
| WO | 2007/069666 A1 | 6/2007 |
| WO | 2007/097494 A1 | 8/2007 |
| WO | 2008/030610 A2 | 3/2008 |
| WO | 2008/038148 A2 | 4/2008 |
| WO | 2008/105630 A1 | 9/2008 |

(Continued)

OTHER PUBLICATIONS

Takahashi et al., "Induction of Pluripotent Stem Cells from Mouse Embryonic and Adult Fibroblast Cultures by Defined Factors" *Cell* 126(4):663-76, published online Aug. 10, 2006.
Takahashi et al., "Induction of Pluripotent Stem Cells from Adult Human Fibroblasts by Defined Factors" *Cell* 131(5):861-72, published online Nov. 20, 2007.
Yu et al., "Induced Pluripotent Stem Cell Lines Derived from Human Somatic Cells" *Science* 318(5858):1917-20, published online Nov. 20, 2007.
Park et al., "Reprogramming of human somatic cells to pluripotency with defined factors" *Nature* 451:141-46, published online Dec. 23, 2007.
*Jikken Igaku* (*Experimental Medicine*) 24:814-19, 2006, along with an English language translation thereof.

(Continued)

*Primary Examiner* — Thaian N Ton
(74) *Attorney, Agent, or Firm* — Foley & Lardner LLP

(57) ABSTRACT

This relates to a method of preparing induced pluripotent stem cells, comprising a nuclear reprogramming step with a nuclear reprogramming factor in the presence of miRNA, wherein said miRNA has a property of providing a higher nuclear reprogramming efficiency in the presence of said miRNA than in the absence thereof.

9 Claims, 16 Drawing Sheets
(13 of 16 Drawing Sheet(s) Filed in Color)

(56) References Cited

FOREIGN PATENT DOCUMENTS

| WO | 2008/118820 A2 | 10/2008 |
| WO | 2008/124133 A1 | 10/2008 |
| WO | 2008/151058 A2 | 12/2008 |
| WO | 2009/006930 A1 | 1/2009 |
| WO | 2009/006997 A1 | 1/2009 |
| WO | 2009/007852 A2 | 1/2009 |
| WO | 2009/032456 A2 | 3/2009 |
| WO | 2009/057831 A1 | 5/2009 |

OTHER PUBLICATIONS

*microRNA Jikken Purotokoru (miroRNA Experimental Protocol)*, pp. 20-35, 2008, Yodosha Co., Ltd.
Ying et al., "The MicroRNA: Overview of the RNA Gene That Modulates Gene Functions," *Methods in Molecular Biology, MicroRNA Protocols*, vol. 342, pp. 1-18, Humana Press, 2006.
Houbaviy et al., "Embryonic Stem Cell-Specific MicroRNAs" *Developmental Cell* 5(2):351-58, 2003.
Sinkkonen et al., "MicroRNAs control de novo DNA methylation through regulation of transcriptional repressors in mouse embryonic stem cells" *Nat. Struct. Mol. Biol.* 15(3):259-267, published online Mar. 2, 2008.
Benetti et al., "A mammalian microRNA cluster controls DNA methylation and telomere recombination via Rbl2-dependent regulation of DNA methyltransferases" *Nat. Struct. Mol. Biol.* 15(3):268-79, published online Mar. 2, 2008.
Griffiths-Jones et al., "miRBase: tools for microRNA genomics" *Nucleic Acids Research* 36:D154-D158, published online Nov. 8, 2007.
Stadtfeld et al., "Induced pluripotent stem cells generated without viral integration" *Science* 322(5903):945-49, published online Sep. 25, 2008.
Okita et al., "Generation of mouse induced pluripotent stem cells without viral vectors" *Science* 322(5903):949-53, published online Oct. 9, 2008.
Yamanaka, "Pluripotency of differentiation and miRNA" *The Journal of Biochemistry*, vol. 79, No. 11, Abstract 3BT17 from the 80th Annual Meeting of the Japanese Biochemical Society, Nov. 25, 2007, along with an English language translation thereof.
Koyanagi et al., "Screening and functional analysis of microRNAs which involve in reprogramming of murine somatic cells" *The Journal of Biochemistry*, vol. 79, No. 11, Abstract 1T7-7 from the 80th Annual Meeting of the Japanese Biochemical Society, Nov. 25, 2007, along with an English language translation thereof.
Zhang et al., "MicroRNA: A New Player in Stem Cells" *Journal of Cellular Physiology* 209:266-269, 2006.
Spivakov et al., "Epigenetic signatures of stem-cell identity" *Nat. Rev. Genet.* 8(4):263-271, 2007.
Suh et al., "Human embryonic stem cells express a unique set of microRNAs" *Developmental Biology* 270:488-498, 2004.
Hatfield et al., "Stem cell division is regulated by the microRNA pathway" *Nature* 435(7044):974-978, 2005.
Kanellopoulou et al., "Dicer-deficient mouse embryonic stem cells are defective in differentiation and centromeric silencing" *Genes & Development* 19:489-501, 2005.
Bang et al., "Deconstructing Pluripotency" *Science* 320:58-59, 2008.
Viswanathan et al., "Selective Blockade of MicroRNA Processing by Lin28" *Science* 320:97-100, 2008.
Adewumi et al., "Characterization of human embryonic stem cell lines by the International Stem Cell Initiative" *Nat. Biotechnol.* 25(7):803-16, 2007.
Adhikary et al., "Transcriptional regulation and transformation by Myc proteins" *Nat. Rev. Mol. Cell Biol.* 6:635-45, 2005.
Akimov et al., "Bypass of Senescence, Immortalization, and Transformation of Human Hematopoietic Progenitor Cells" *Stem Cells* 23:1423-33, 2005.

Amit et al., "Clonally Derived Human Embryonic Stem Cell Lines Maintain Pluripotency and Proliferative Potential for Prolonged Periods of Culture" *Dev. Biol.* 227:271-78, 2000.
Aoi et al., "Generation of pluripotent stem cells from adult mouse liver and stomach cells" *Science* 321(5889):699-702, published online Feb. 14, 2008.
*Asahi Shimbun Weekly AERA* "The novel pluripotent cells established by Professor Yamanaka of Kyoto University may change medical care" pp. 72-73, Dec. 24, 2007, along with a partial English language translation thereof.
Avilion et al., "Multipotent cell lineages in early mouse development depend on SOX2 function" *Genes Dev.* 17:126-40, 2003.
Brambrink et al., "Sequential expression of pluripotency markers during direct reprogramming of mouse somatic cells" *Cell Stem Cell* 2(2):151-59, 2008.
Barrett et al. "Activation Domains of L-Myc and c-Myc Determine Their Transforming Potencies in Rat Embryo Cells" *Mol. Cell. Biol.* 12(7):3130-37, 1992.
Ben-Shushan et al., "*Rex-1*, a Gene Encoding a Transcription Factor Expressed in the Early Embryo, Is Regulated via Oct-3/4 and Oct-6 Binding to an Octomer Site and a Novel Protein, Rox-1, Binding to an Adjacent Site" *Mol. Cell Biol.* 18(4):1866-78, 1998.
Birrer et al., "L-myc Cooperates with *ras* to Transform Primary Rat Embryo Fibroblasts" *Mol. Cell. Biol.* 8(6):2668-73, 1988.
Blackwood et al., "Max: a helix-loop-helix zipper protein that forms a sequence-specific DNA-binding complex with Myc" *Science* 251(4998):1211-17, 1991.
Blelloch et al., "Generation of Induced Pluripotent Stem Cells in the Absence of Drug Selection" *Cell Stem Cell* 1(3):245-247, 2007.
Block et al., "Population Expansion, Clonal Growth, and Specific Differentiation Patterns in Primary Cultures of Hepatocytes Induced by HGF/SF, EGF and TGFα in a Chemically Defined (HGM) Medium" *J. Cell Biol.* 132(6):1133-49, 1996.
Bortvin et al., "Incomplete reactivation of *Oct4*-related genes in mouse embryos cloned from somatic nuclei" *Development* 130:1673-80, 2003.
Boyer et al., "Core Transcriptional Regulatory Circuitry in Human Embryonic Stem Cells" *Cell* 122:947-56, 2005.
Brough et al., "An Essential Domain of the c-Myc Protein Interacts with a Nuclear Factor That Is Also Required for E1A-Mediated Transformation" *Mol. Cell. Biol.* 15(3):1536-44, 1995.
Cartwright et al., "LIF/STAT3 controls ES cell self-renewal and pluripotency by a Myc-dependent mechanism" *Development* 132:885-96, 2005.
Chambers et al., "Functional Expression Cloning of Nanog, a Pluripotency Sustaining Factor in Embryonic Stem Cells" *Cell* 113:643-55, 2003.
Check, E. "Simple Recipe Gives Adult Cells Embryonic Powers" *Nature* 442:11, Jul. 6, 2006.
Cheng et al., "Mammalian Grb2 Regulates Multiple Steps in Embryonic Development and Malignant Transformation" *Cell* 95:793-803, 1998.
Cowan et al., "Derivation of Embryonic Stem-Cell Lines from Human Blastocysts" *N. Engl. J. Med.* 350:1353-56, 2004.
Cowan et al., "Nuclear Reprogramming of Somatic Cells After Fusion with Human Embryonic Stem Cells" *Science* 309:1369-73, 2005.
Cyranoski et al., "Simple Switch Turns Cells Embryonic" *Nature* 447:618-619, Jun. 7, 2007.
Correction printed in *Nature* 447:897, Jun. 21, 2007.
Dang et al., "The biology of the mammalian Krüppel-like family of transcription factors" *Int. J. Biochem. Cell Biol.* 32:1103-21, 2000.
Evans et al., "Establishment in culture of pluripotential cells from mouse embryos" *Nature* 292:154-56, 1981.
Evans et al., "Krüppel-like Factor 4 is Acetylated by p300 and Regulates Gene Transcription via Modulation of Histone Acetylation" *J. Biol. Chem.* 282(47):33994-34002, 2007.
Ghaleb et al., "Krüppel-like factors 4 and 5: the yin and yang regulators of cellular proliferation" *Cell Res.* 15(2):92-96, 2005.
Hanna et al., "Treatment of sickle cell anemia mouse model with iPS cells generated from autologous skin" *Science* 318(5858):1920-23, published online Dec. 6, 2007.

(56) References Cited

OTHER PUBLICATIONS

Hanna et al., "Direct Reprogramming of Terminally Differentiated Mature B Lymphocytes to Pluripotency" *Cell* 133:250-64, Apr. 17, 2008.

Hasegawa et al., "Efficient Multicistronic Expression of a Transgene in Human Embryonic Stem Cells" *Stem Cells* 25:1707-12, 2007.

Herold et al. "Negative Regulation of the Mammalian UV Response by Myc through Association with Miz-1" *Mol. Cell* 10(3):509-21, 2002.

Horikawa et al., "Differential cis-regulation of human versus mouse TERT gene expression in vivo: Identification of a human-specific repressive element" *Proc. Natl. Acad. Sci. U.S.A.* 102(51):18437-42, 2005.

Hsiao et al., "Marking Embryonic Stem Cells with a 2A Self-Cleaving Peptide: A NKX2-5 Emerald GFP BAC Reporter" *PLoS ONE* 3(7):e2532, 2008.

Huangfu et al., "Induction of pluripotent stem cells by defined factors is greatly improved by small-molecule compounds" *Nature Biotechnology* 26(7):795-97, 2008.

Humphries, C. "Reprogrammed Stem Cells Work on Parkinson's: A study in rodents suggests that skin cells can be transformed into neurons to treat neurodegeneration" *Technology Review*, published by MIT, Apr. 8, 2008. http:///www.technologyreview.com/printer_friendly_article.aspx?id=20530.

Hwang et al., "Evidence of a Pluriportent Human Embryonic Stem Cell Line Derived from a Cloned Blastocyst" *Science* 303:1669-74, 2004.

Hwang et al., "Patient-Specific Embryonic Stem Cells Derived from Human SCNT Blastocysts" *Science* 308:1777-83, 2005.

Itskovitz-Eldor et al., "Differentiation of Human Embryonic Stem Cells into Embryoid Bodies Comprising the Three Embryonic Germ Layers" *Mol. Med.* 6(2):88-95, 2000.

Kawasaki et al., "Induction of Midbrain Dopaminergic Neurons from ES Cells by Stromal Cell-Derived Inducing Activity" *Neuron* 28:31-40, 2000.

Kohlhase et al., "Cloning and expression analysis of *Sall4*, the murine homologue of the gene mutated in Okihiro syndrome" *Cytogenet. Genome Res.* 98:274-77, 2002.

Kubicek et al., "Reversal of H3K9me2 by a Small-Molecule Inhibitor for the G9a Histone Methyltransferase" *Molecular Cell* 25:473-81, 2007.

*Kyoto Shimbun* (Japanese Newspaper) article of Apr. 16, 2008, columns 1-3, along with a partial English language translation thereof.

Laflamme et al., "Cardiomyocytes derived from human embryonic stem cells in pro-survival factors enhance function of infarcted rat hearts" *Nat. Biotechnol.* 25(9):1015-24, 2007.

Li et al., "Leukaemia disease genes: large-scale cloning and pathway predictions" *Nat. Genet.* 23(3):348-353, 1999.

Lin et al., "Mir-302 reprograms human skin cancer cells into a pluripotent ES-cell-like state" *RNA* 14:1-10, 2008.

Liao et al., "Enhanced Efficiency of Generating Induced Pluripotent Stem (iPS) Cells from Human Somatic Cells by a Combination of Six Transcription Factors" *Cell Research* 18:600-603, doi: 10.1038/cr.2008.51, published online Apr. 15, 2008.

Loh et al., "The Oct4 and Nanog transcription network regulates pluripotency in mouse embryonic stem cells" *Nat. Genet.* 38(4):431-40, 2006.

Loriot et al., "Five new human cancer-germline genes identified among 12 genes expressed in spermatogonia." *Int. J. Cancer* 105:371-76, 2003.

Lowry et al., "Generation of human induced pluripotent stem cells from dermal fibroblasts" *Proc. Natl. Acad. Sci. U.S.A.* 105(8):2883-88, 2008.

Maherali et al., "Directly Reprogrammed Fibroblasts Show Global Epigenetic Remodeling and Widespread Tissue Contribution" *Cell Stem Cell* 1:55-70, 2007.

Mali et al., "Improved Efficiency and Pace of Generating Induced Pluripotent Stem Cells from Human Adult and Fetal Fibroblasts" *Stem Cells*, published online May 29, 2008, DOI:10.1634/stemcells. 2008-0346.

Marson et al., "Wnt Signaling Promotes Reprogramming of Somatic Cells to Pluripotentcy" *Cell Stem Cell* 3:132-35, 2008.

Martin, "Isolation of a pluripotent cell line from early mouse embryos cultured in medium conditioned by teratocarcinoma stem cells" *Proc. Natl. Acad. Sci. USA* 78(12):7634-38, 1981.

Maruyama et al., "Differential Roles for Sox15 and Sox2 in Transcriptional Control in Mouse Embryonic Stem Cells" *J. Biol. Chem.* 280(26):24371-79, 2005.

Masaki et al., "Heterogeneity of pluripotent marker gene expression in colonies generated in human iPS cell induction culture" *Stem Cell Res.* (2008) DOI:10.1016/j.scr.2008.01.001.

Matsuda et al., "STAT3 activation is sufficient to maintain an undifferentiated state of mouse embryonic stem cells" *EMBO J.* 18(15):4261-69, 1999.

McMahon et al., "The *Wnt*-1 (*int*-1) Proto-Oncogene Is Required for Development of a Large Region of the Mouse Brain" *Cell* 62:1073-85, 1990.

Meiner et al., "Disruption of the acyl-CoA:cholesterol acyltransferase gene in mice: Evidence suggesting multiple cholesterol esterification enzymes in mammals" *Proc. Natl. Acad. Sci. USA* 93:14041-46, 1996.

Meissner et al., "Direct reprogramming of genetically unmodified fibroblasts into pluripotent stem cells" *Nat. Biotechnol.* 25(10):1177-1181, published online Aug. 27, 2007.

Mitsui et al., "The Homeoprotein Nanog Is Required for Maintenance of Pluripotency in Mouse Epiblast and ES cells" *Cell* 113:631-42, 2003.

Morita et al., "Plat-E: an efficient and stable system for transient packaging of retroviruses" *Gene Ther.* 7:1063-66, 2000.

Nakagawa et al., "Generation of induced pluripotent stem cells without Myc from mouse and human fibroblasts" *Nat. Biotechnol.* 26(1):101-06, published online Nov. 30, 2007.

*Newton* "Attracting world's attention. Pluripotent cells are generated from human skin. What is the 'iPS cell' that can be used not only in the regeneration therapy but also in the tailor-made therapy" pp. 70-75, Feb. 2008, along with a partial English language translation thereof.

Nichols et al., "Formation of Pluripotent Stem Cells in the Mammalian Embryo Depends on the POU Transcription Factor Oct4" *Cell* 95:379-91, 1998.

Nienhuis et al., "Genotoxicity of retroviral integration in hematopoietic cells" *Mol. Ther.* 13(6):1031-49, 2006.

Niwa et al., "Efficient selection for high-expression transfectants with a novel eukaryotic vector" *Gene* 108(2):193-99, 1991.

Niwa et al., "Self-renewal of pluripotent embryonic stem cells is meditated via activation of STAT3" *Genes Dev.* 12:2048-60, 1998.

Nolta et al., "Transduction of pluripotent human hematopoietic stem cells demonstrated by clonal analysis after engraftment in immune-deficient mice" *Proc. Natl. Acad. Sci. USA* 93:2414-19, 1996.

Okamoto et al., "A Novel Octamer Binding Transcription Factor is Differentially Expressed in Mouse Embryonic Cells" *Cell* 60:461-72, 1990.

Okita et al., "Generation of germline-competent induced pluripotent stem cells" *Nature* 448:313-17, 2007.

Okuda et al., "UTF1, a novel transcriptional coactivator expressed in pluripotent embryonic stem cells and extra-embryonic cells" *EMBO J.* 17(7):2019-32, 1998.

Postic et al., "Dual Roles for Glucokinase in Glucose Homeostasis as Determined by Liver and Pancreatic β Cell-specific Gene Knockouts Using Cre Recombinase" *J. Biol. Chem.* 274(1):305-15, 1999.

Qin et al., "Direct generation of ES-like cells from unmodified mouse embryonic fibroblasts by Oct4/Sox2/Myc/Klf4" *Cell Res.* 17(11):959-62, 2007.

Rao, "Conserved and divergent paths that regulate self-renewal in mouse and human embryonic stem cells" *Dev. Biol.* 275:269-86, 2004.

Ryan et al., "POU domain family values: flexibility, partnerships, and developmental codes" *Genes Dev.* 11:1207-25, 1997.

(56) References Cited

OTHER PUBLICATIONS

Sakai et al., "A Transgenic Mouse Line That Retains Cre Recombinase Activity in Mature Oocytes Irrespective of the *cre* Transgene Transmission" *Biochem. Biophys. Res. Commun.* 237(2):318-24, 1997.
Salmon et al., "Reversible Immortalization of Human Primary Cells by Lentivector-Mediated Transfer of Specific Genes" *Mol. Ther.* 2(4):404-14, 2000.
Sato et al., "Maintenance of pluripotency in human and mouse embryonic stem cells through activation of Wnt signaling by a pharmacological GSK-3-specific inhibitor" *Nat. Med.* 10(1):55-63, 2004.
Schepers et al., "Twenty Pairs of *Sox*: Extent, Homology, and Nomenclature of the Mouse and Human Sox Transcription Factor Gene Families" *Dev. Cell* 3:167-70, 2002.
Shi et al., "A Combined Chemical and Genetic Approach for the Generation of Induced Pluripotent Stem Cells" *Cell Stem Cell* 2:525-28, 2008.
Shi et al., "Induction of Pluripotent Stem Cells from Mouse Embryonic Fibroblasts by Oct4 and Klf4 with Small-Molecule Compounds" *Cell Stem Cell* 3:568-74, 2008.
Silva et al., "Promotion of Reprogramming to Ground State Pluripotency by Signal Inhibition" *PLoS Biology* 6(10):2237-47, 2008.
Spencer et al., "E-Cadherin Inhibits Cell Surface Localization of the Pro-Migratory 5T4 Oncofetal Antigen in Mouse Embryonic Stem Cells" *Mol. Biol. Cell* 18:2838-51, 2007.
Stadtfeld et al., "Defining Molecular Cornerstones during Fibroblast to iPS Cell Reprogramming in Mouse" *Cell Stem Cell* 2(3):230-40, 2008.
"Stem cells made to mimic disease" BBC News, http://newsvote.bbc.co.uk/mpapps/pagetools/print/news.bbc.co.uk/2/hi/health/7334365.stm, Apr. 7, 2008.
Sumi et al., "Apoptosis and differentiation of human embryonic stem cells induced by sustained activation of c-Myc" *Oncogene* 26:5564-76, 2007.
Surani et al., "A New Route to Rejuvenation" *Nature* 443:284-285, Sep. 21, 2006.
Tada et al., "Nuclear reprogramming of somatic cells by in vitro hybridization with ES cells" *Current Biology* 11(19):1553-58, 2001.
Takahashi et al., "Role of ERas in promoting tumour-like properties in mouse embryonic stem cells" *Nature* 423:541-45, 2003.
Takahashi et al., "Induction of pluripotent stem cells from fibroblast cultures" *Nat. Protocols* 2(12):3081-89, published online Nov. 29, 2007.
Takahashi et al., "Induced Pluripotent Stem Cells" *Jikken Igaku (Experimental Medicine)* 26(5):35-40, 2008.
Takeda et al., "Human Oct3 gene family: cDNA sequences, alternative splicing, gene organization, chromosomal location, and expression at low levels in adult tissues" *Nucleic Acids Research* 20(17):4613-4620, 1992.
Taranger et al., "Induction of Dedifferentiation, Genomewide Transcriptional Programming, and Epigenetic Reprogramming by Extracts of Carcinoma and Embryonic Stem Cells" *Mol. Biol. Cell* 16:5719-35, 2005.
Tateno et al., "Heterogeneity of growth potential of adult rat hepatocytes in vitro" *Hepatology* 31(1):65-74, 2000.
Thomson et al., "Embryonic Stem Cell Lines Derived from Human Blastocysts" *Science* 282:1145-47, 1998.
Tokuzawa et al., "Fbx15 Is a Novel Target of Oct3/4 but is Dispensable for Embryonic Stem Cell Self-Renewal and Mouse Development" *Mol. Cell Biol.* 23(8): 2699-708, 2003.
Verrey et al., "CATs and HATs: the SLC7 family of amino acid transporters" *Pflügers Archiv-European Journal of Physiology*, DOI 10.1007/s00424-003-1086-z, pp. 1-23, published online Jun. 11, 2003.
Vintersten et al., "Mouse in Red: Red Fluorescent Protein Expression in Mouse ES Cells, Embryos, and Adult Animals" *Genesis* 40:241-46, 2004.
Wakayama et al., "Full-term development of mice from enucleated oocytes injected with cumulus cell nuclei" *Nature* 394:369-74, 1998.
Wang et al., "A protein interaction network for pluripotency of embryonic stem cells" *Nature* 444:364-68, 2006.
Wernig et al., "In vitro reprogramming of fibroblasts into a pluripotent ES-cell-like state" *Nature* 448:318-24, 2007.
Wernig et al., "c-Myc is dispensable for direct reprogramming of mouse fibroblasts" *Cell Stem Cell* 2(1):10-12, published online Dec. 13, 2007.
Wernig et al., "Neurons derived from reprogrammed fibroblasts functionally integrate into the fetal brain and improve symptoms of rats with Parkinson's disease" *Proc. Natl. Acad. Sci. USA* 105(15):5856-5861, 2008.
Wilmut et al., "Viable offspring derived from fetal and adult mammalian cells" *Nature* 385:810-13, 1997.
Xu et al., "Basic FGF and suppression of BMP signaling sustain undifferentiated proliferation of human ES cells" *Nat. Methods* 2(3):185-90, 2005.
Yamanaka et al., "Mouse Sen'iga Saibo Kara Yudo Tanosei Kansaibo o Tsukuru (Induction of pluripotent stem cells from mouse fibroblast cultures)" *Tanpakushitsu Kakusan Koso (Protein, Nucleic Acid and Enzyme)* 51(15):2346-51, 2006.
Yamanaka, "Strategies and New Developments in the Generation of Patient-Specific Pluripotent Stem Cells" *Cell Stem Cell* 1:39-49, 2007.
Yang et al., "Nuclear reprogramming of cloned embryos and its implications for therapeutic cloning" *Nat. Genet.* 39(3):295-302, 2007.
Ying et al., "BMP Induction of Id Proteins Suppresses Differentiation and Sustains Embryonic Stem Cell Self-Renewal in Collaboration with STAT3" *Cell* 115:281-92, 2003.
Zhao et al., "Two Supporting Factors Greatly Improve the Efficiency of Human iPSC Generation" *Cell Stem Cell* 3:475-79, 2008.
English language Abstract of JP 2002-065261, Mar. 5, 2002.
English language Abstract of JP 2003-009854, Jan. 14, 2003.
English language Abstract of JP 2004-161682, Jun. 10, 2004.
English language Abstract of JP 2005-095027, Apr. 14, 2005.
English language Abstract of JP 2008-283972, Nov. 27, 2008.
U.S. Appl. No. 12/289,873, filed Nov. 6, 2008 to Yamanaka et al., entitled "Nuclear Reprogramming Factor and Induced Pluripotent Stem Cells."
U.S. Appl. No. 12/292,717, filed Nov. 25, 2008 to Yamanaka et al., entitled "Efficient Method for Nuclear Reprogramming."
U.S. Appl. No. 12/457,356, filed Jun. 9, 2009 to Yamanaka, entitled "Nuclear Reprogramming Factor and Induced Pluripotent Stem Cells."
Kim et al., "Generation of Human Induced Pluripotent Stem Cells by Direct Delivery of Reprogramming Proteins" *Cell Stem Cell* 4:472-476, 2009.
Ziegler et al., "The Cationic Cell-Penetrating Peptide CPP$^{TAT}$ Derived from the HIV-1 Protein TAT Is Rapidly Transported into Living Fibroblasts: Optical, Biophysical, and Metabolic Evidence" *Biochemistry* 44:138-148, published online Dec. 14, 2004.
Zhou et al., "Generation of Induced Pluripotent Stem Cells Using Recombinant Proteins" *Cell Stem Cell* 4:381-384, 2009.
Wadia et al., "Protein Transduction Technology" *Curr. Opin. Biotechnol.* 13:52-56, 2002.
Cosmo Bio News 49:5, 2005 (catalog of ES cell culture medium).
BioPorter™ Gene Therapy System, Inc., Wako Bio Window 40:7, 2002.
BioPorter™ Protein Delivery Reagent from www.biocarta.com.
Wakayama et al., "Differentiation of Embryonic Stem Cell Lines Generated from Adult Somatic Cells by Nuclear Transfer" *Science* 292:740-43, 2001.
Amsellem et al., "Ex vivo Expansion of Human Hematopoietic Stem Cells by Direct Delivery of the HOXB4 Homeoprotein" *Nat. Med.* 9(11):1423-27, 2003.
Krosl et al., "In vitro Expansion of Hematopoietic Stem Cells by Recombinant TAT-HOXB4 Protein" *Nat. Med.* 9( 11):1428-32, 2003.
Kim et al., "Oct4-Induced Pluripotency in Adult Neural Stem Cells" *Cell* 136:411-419, 2009.

(56) References Cited

OTHER PUBLICATIONS

Kim et al., "Pluripotent Stem Cells Induced From Adult Neural Stem Cells by Reprogramming with Two Factors" *Nature* 454:646-650, 2008.

Huangfu et al., "Induction of Pluripotent Stem Cells From Primary Human Fibroblasts with Only *Oct4* and *Sox 2*" *Nature Biotechnology* 26:1269-1275, 2008.

Feng et al., "Reprogramming of Fibroblasts into Induced Pluripotent Stem Cells with Orphan Nuclear Receptor Esrrb" *Nature Cell Biology* 11:197-203, 2009.

Mali et al. "Improved Efficiency and Pace of Generating Induced Pluripotent Stem Cells from Human Adult and Fetal Fibroblasts" *Stem Cells* 26:1998-2005, 2008.

Yu et al., "Human Induced Pluripotent Stem Cells Free of Vector and Transgene Sequences" *Science* 324:797-801, 2009.

Wei et al., "Characterization and Comparative Profiling of the Small RNA Transcriptomes in Two Phases of Locust" *Genome Biology*, vol. 10, Issue 1, Article R6, 2009.

Griffiths-Jones et al., "miRBase: microRNA Sequences, Targets and Gene Nomenclature" *Nucleic Acids Research*, vol. 34, D140-144, 2006.

Gonzalez et al., "Generation of Mouse-Induced Pluripotent Stem Cells by Transient Expression of a Single Nonviral Polycistronic Vector" *Proc. Natl. Acad. Sci. USA*, vol. 106, No. 22, pp. 8918-8922, 2009.

Warren et al., "Highly Efficient Reprogramming to Pluripotency and Directed Differentiation of Human Cells with Synthetic Modified mRNA" *Cell Stem Cell*, vol. 7, pp. 618-630, 2010.

Aasen et al., "Efficient and Rapid Generation of Induced Pluripotent Stem Cells from Human Keratinocytes" *Nat. Biotechnol.*, vol. 26, No. 11, pp. 1276-1284, published online Oct. 17, 2008.

Stadtfeld et al., "Reprogramming of Pancreatic β Cells into Induced Pluripotent Stem Cells" *Curr. Biol.*, vol. 18, No. 12, 2008 (11 pages).

Card et al., "Oct4/Sox2-Regulated miR-302 Targets Cyclin D1 in Human Embryonic Stem Cells" Molecular and Cellular Biology, vol. 28, No. 20, pp. 6426-6438, XP002577530, Oct. 2008.

Lin et al., "Role of mir-302 MicroRNA Family in Stem Cell Pluripotency and Renewal" Current Perspectives in Micrornas (MIRNA), Springer Netherlands, pp. 167-185, XP009121067, Aug. 1, 2008.

Tay et al., "MicroRNAs to Nanog, Oct4 and Sox2 Coding Regions Modulate Embryonic Stem Cell Differentiation" Nature, vol. 455, No. 7216, pp. 1124-1128, XP002577531, Oct. 23, 2008.

Laurent et al., "Comprehensive MicroRNA Profiling Reveals a Unique Human Embryonic Stem Cell Signature Dominated by a Single Seed Sequence" Stem Cells, vol. 26, No. 6, XP002577532, pp. 1506-1516, published online Apr. 10, 2008.

Marson et al., "Connecting MicroRNA Genes to the Core Transcriptional Regulatory Circuitry of Embryonic Stem Cells" Cell, vol. 134, No. 3, pp. 521-533, XP002577533, Aug. 8, 2008.

Judson et al., "Embryonic Stem Cell-Specific MicroRNAs Promote Induced Pluripotency" Nature Biotechnology, vol. 27, No. 5, pp. 459-461, XP002577534, published online Apr. 12, 2009.

Fig. 6
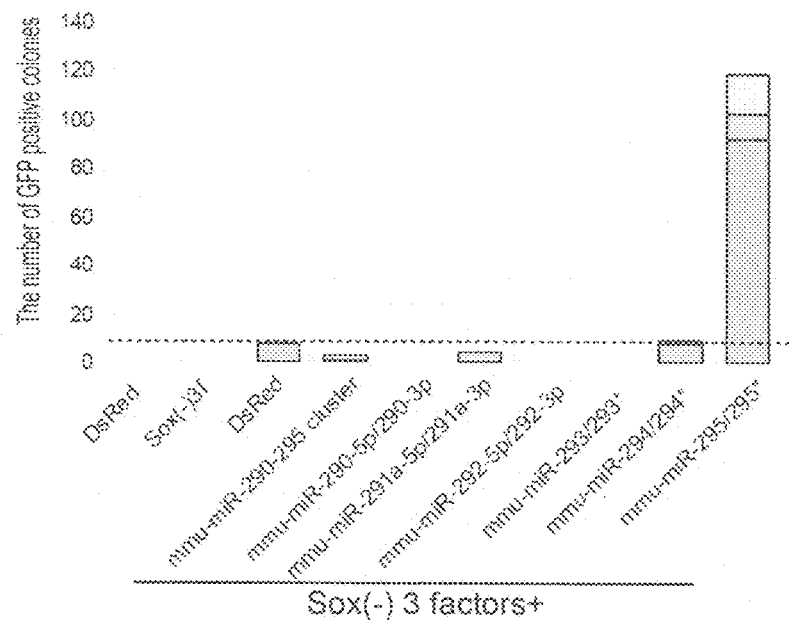
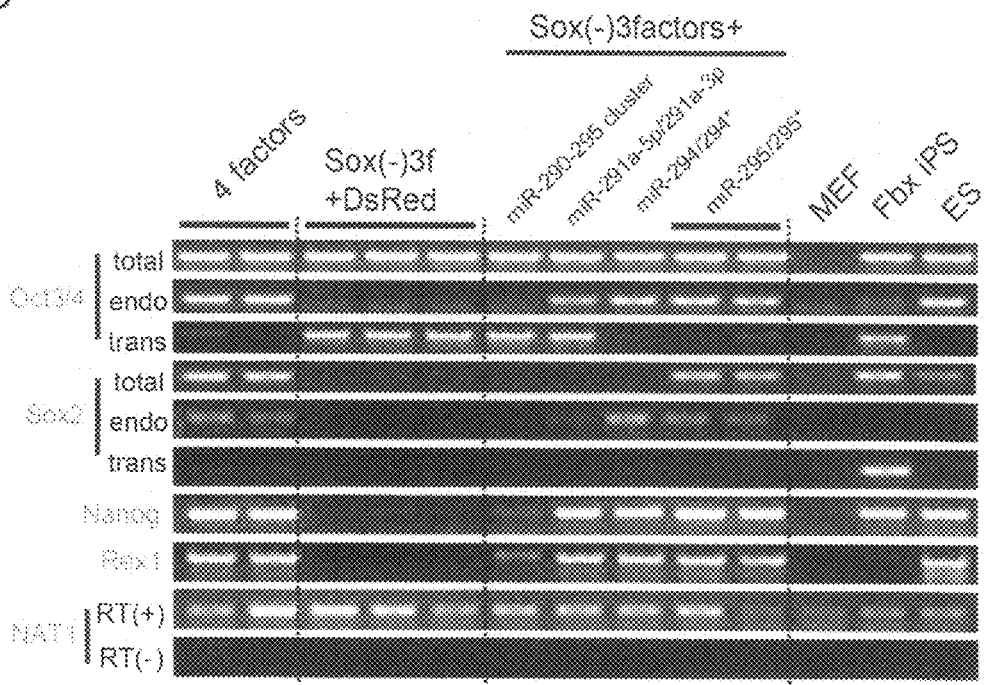

Fig. 7
A
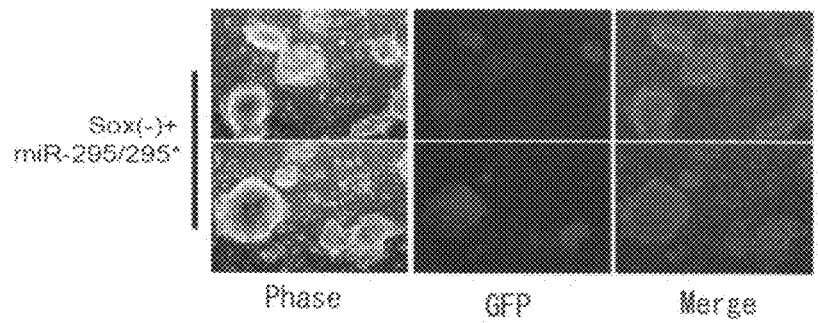
B
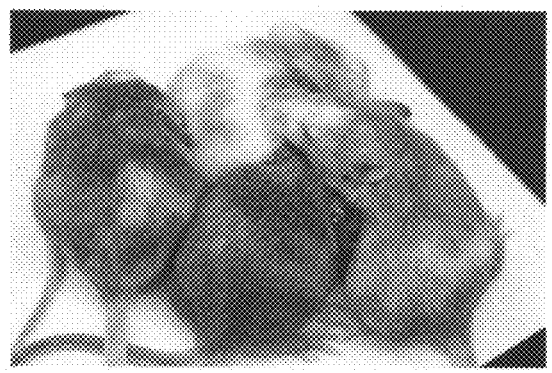
C
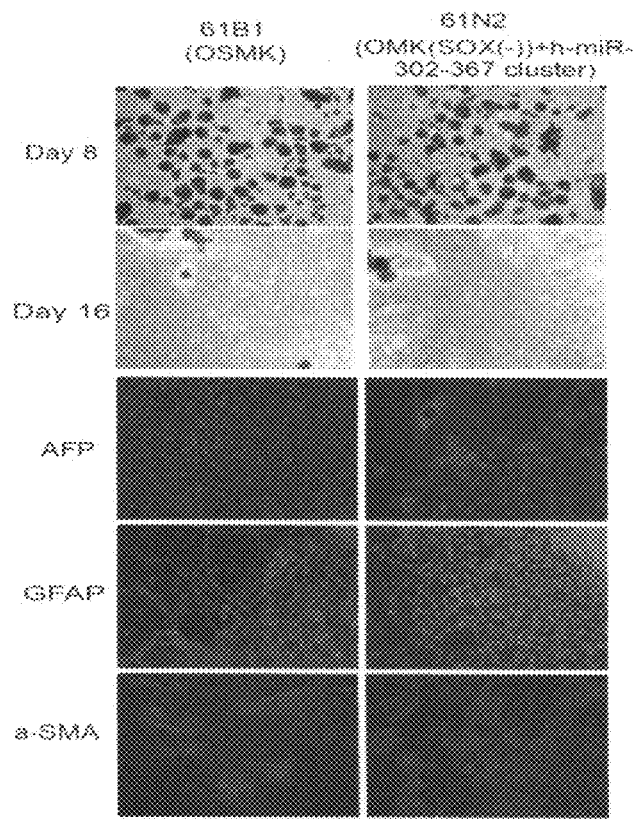

Fig. 8
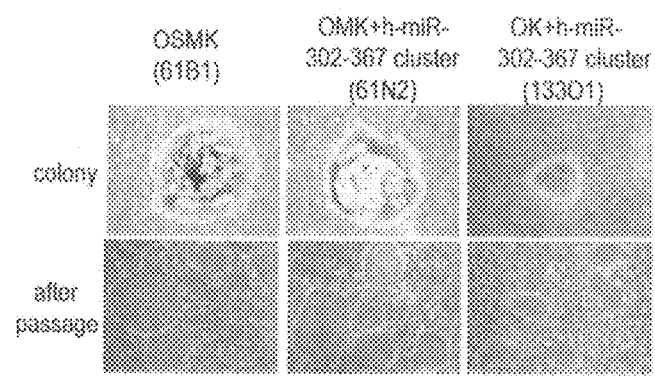
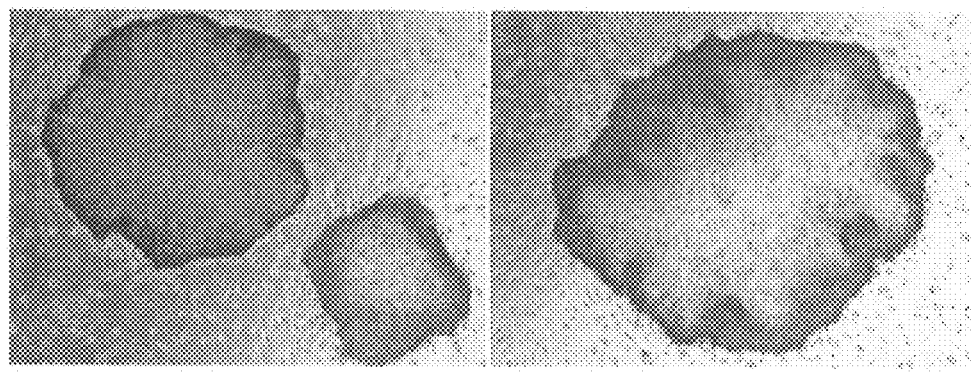

SEQUENCE LISTING

```
<160> NUMBER OF SEQ ID NOS: 14

<210> SEQ ID NO 1
<211> LENGTH: 84
<212> TYPE: RNA
<213> ORGANISM: Mus musculus

<400> SEQUENCE: 1
uuccauauag ccauacucaa aauggaggcc cuaucuaagc uuuuaagugg aaagugcuuc      60
ccuuuugugu guugccaugu ggag                                            84

<210> SEQ ID NO 2
<211> LENGTH: 69
<212> TYPE: RNA
<213> ORGANISM: Mus musculus

<400> SEQUENCE: 2
ggugagacuc aaaugugggg cacacuucug gacuguacau agaaagugcu acuacuuuug      60
agucucucc                                                             69

<210> SEQ ID NO 3
<211> LENGTH: 67
<212> TYPE: RNA
<213> ORGANISM: Homo sapiens

<400> SEQUENCE: 3
```

```
gugggccuca aaugugagc acuauucuga uguccaagug gaaagugcug cgacauuuga    60
gcgucac                                                            67

<210> SEQ ID NO 4
<211> LENGTH: 69
<212> TYPE: RNA
<213> ORGANISM: Homo sapiens

<400> SEQUENCE: 4
gggauacuca aaauggggc gcuuccuuu uugucuguac ugggaagugc uucgauuug     60 ggugucccc                                                          69

<210> SEQ ID NO 5
<211> LENGTH: 73
<212> TYPE: RNA
<213> ORGANISM: Homo sapiens

<400> SEQUENCE: 5
gcucccuuca acuuaacau ggaagugcuu ucugugacuu uaaaaguaag ugcuuccaug    60
uuuuaguagg agu                                                     73

<210> SEQ ID NO 6
<211> LENGTH: 68
<212> TYPE: RNA
<213> ORGANISM: Homo sapiens

<400> SEQUENCE: 6
ccuuugcuuu aacauggggg uaccugcugu gugaaacaaa aguaagugcu uccauguuuc   60
aguggagg                                                           68

<210> SEQ ID NO 7
<211> LENGTH: 69
<212> TYPE: RNA
<213> ORGANISM: Homo sapiens

<400> SEQUENCE: 7
ccaccacuua aacguggaug uacuugcuuu gaaacuaaag aaguaagugc uuccauguuu   60
uggugaugg                                                          69

<210> SEQ ID NO 8
<211> LENGTH: 68
<212> TYPE: RNA
<213> ORGANISM: Homo sapiens

<400> SEQUENCE: 8
ccucuacuuu aacauggagg cacuugcugu gacaugacaa aaauaagugc uuccauguuu   60
gagugugg                                                           68

<210> SEQ ID NO 9
<211> LENGTH: 68
<212> TYPE: RNA
<213> ORGANISM: Homo sapiens

<400> SEQUENCE: 9
ccauuacugu ugcuaauaug caacucuguu gaauauaaau uggaauugca cuuuagcaau   60
ggugaugg                                                           68

<210> SEQ ID NO 10
```

```
<211> LENGTH: 87
<212> TYPE: RNA
<213> ORGANISM: Homo sapiens

<400> SEQUENCE: 10
ucucaggcug ucguccucua gagggaagca cuuucuguug ucugaaagaa aagaaagugc      60
uuccuuuuag aggguuaccg uuugaga                                         87

<210> SEQ ID NO 11
<211> LENGTH: 82
<212> TYPE: RNA
<213> ORGANISM: Mus musculus

<400> SEQUENCE: 11
ccuauguagc ggccaucaaa guggaggccc ucucuugagc cugaaugaga aagugcuucc      60
acuuugugug ccacugcaug gg                                              82

<210> SEQ ID NO 12
<211> LENGTH: 820
<212> TYPE: RNA
<213> ORGANISM: Homo sapiens

<400> SEQUENCE: 12
guuuucuuuc uccucagcuc uaaauacucu gaaguccaaa gaaguuguau guugggaggg      60
cucccuucaa cuuuaacaug gaagugcuuu cugugacuuu aaaaguaagu gcuuccaugu     120
uuuaguagga gugaauccaa uuuacuucuc caaauagaa cacgcuaacc ucauugaag      180 ggaucccccuu ugcuuaaca uggggguacc ugcugugugc aacaaaagua agugcuucca     240
uguuucagug gaggugcuc caagccagca caccuuuugu acaaaauuuu uuuguuauu      300 guguuuuaag guuacuaagc uuguuacagg uuaaaggauu cuaacuuuu ccaagacugg     360 gcucccacc acuuaaacgu gggaugacuu gcuugaaac uaagaagua agugcuucca      420 uguuuuuggu augguaaguc uuccuuuuac auuuuuauua uuuuuuuaga aaauaacuuu     480
auuguauuga ccgcagcuca uauauuuaag cuuuauuuug uauuuuuaca ucuguuaagg     540 ggccccccucu acuuaacau ggaggcacuu gcugugacau gacaaaaaua agugcuucca      600
uguuugagug uggugguucc uaccuaauca gcaauugcgu uaacgcccac acuguguuca      660
guucuuggcu acaggccauu acuguugcua auaugcaacu cuguugaaua uaaauuggaa    720
uugcacuuua gcaaugguga uggauuguua agccaaugac agaauuuaaa ccacagacuu    780
acuuugauag cacucuuaau gguauaacuu cuucucccau                          820

<210> SEQ ID NO 13
<211> LENGTH: 83
<212> TYPE: RNA
<213> ORGANISM: Mus musculus

<400> SEQUENCE: 13
cucaucuugc gguacucaaa cuauggggggc acuuuuuuuu uucuuuaaaa agugccgccu      60
aguuuuaagc cccgccgguu gag                                             83

<210> SEQ ID NO 14
<211> LENGTH: 965
<212> TYPE: RNA
<213> ORGANISM: Homo sapiens

<400> SEQUENCE: 14
cuucaacagc ucaucaaggg cuacucucca ccuccuugcu uaaaagccuc uucugauggg      60
```

```
uaagugcuuc cacuugcgau cgccgccuug ccgcaucccc ucagccugug gcacucaaac    120
ugugggggca cuuucugcuc ucuggugaaa gugccgccau cuuuugagug uuaccgcuug    180
agaagacuca accugcggag aagauaccau uuugauuggg ugaggggggcg gguagcagga   240 uggcccuaga cccugccuau ggccguuucc ucgugauaua aauuucuugg ccggggcucu    300
ugcagaugga gcugcucacc cugugggccu caaaugugga gcacuauucu gauguccaag   360
uggaaagugc ugcgacauuu gagcgucacc ggugacgccc auaucaacgg augccgugga   420
gcucggucuu cugcaggaac uaaagagccu gugguuucga uucccagccg gaaacugucu   480
uggguacagg ucccuuacag cgucuggcug uaauggcucc ggaaaaccug gggaagggaa   540
gggggccucc ugggcucuca ccugacacaa cuaagggaau cuggguuaga uggugaaagg   600
aagagaaggu ucagggggcg gcugugcgcc ugcgccgggc gcggcggcuc acaccuguaa   660
ucccagcacg uuggggaggcc gaggcaggcg gaucacgagg ucaggagauc gagaccaucc  720
uggcuaacac ggugaaaccc cgucucuacu aaaaauacaa aaaaugagcc gggcguggug   780
gcgggcgccu guaguccccag cuacuuggga ggcugaggca ggagaauggc gugaacccgg  840
gaggcggagu uugcagugag ccgagaucgc gccaccgcac uccagccugg gcgacagagc   900
aagacucauu cucaaagaaa aaaaaaaaaa aaaacagcag cugugaccaa ggggcuguau   960
gcaca                                                              965
```

EFFICIENT METHOD FOR NUCLEAR REPROGRAMMING

PRIOR RELATED APPLICATIONS

This application is a continuation-in-part of U.S. patent application Ser. No. 12/292,717, filed Nov. 25, 2008, now abandoned which is a continuation-in-part of PCT/JP2008/59586, filed May 23, 2008, which claims priority of U.S. Provisional Application No. 60/996,893, filed Dec. 10, 2007, and which application Ser. No. 12/292,717 also claims priority of U.S. Provisional Application No. 60/996,893, filed Dec. 10, 2007. This application also claims priority of Japanese Patent Application No. 2008-312,745, filed Dec. 8, 2008, and Japanese Patent Application No. 2008-335,129, filed Dec. 26, 2008. The entire disclosures of each of the above-cited applications are considered as being part of this application and are expressly incorporated by reference herein in their entireties.

FIELD OF THE INVENTION

The present invention relates to efficient methods for preparing induced pluripotent stem cells through reprogramming of somatic cells, to induced pluripotent stem cells, to uses of induced pluripotent stem cells and to somatic cells derived by inducing differentiation of said pluripotent cells. The present invention also relates to nuclear reprogramming factors and to miRNAs involved in generating induced pluripotent stem cells. The present invention also relates to screening methods, treatments, and therapies involving the use of induced pluripotent stem cells.

BACKGROUND OF THE INVENTION

Embryonic stem cells (ES cells) are stem cells established from human or mouse early embryos which have a characteristic feature that they can be cultured over a long period of time while maintaining pluripotent ability to differentiate into all kinds of cells existing in living bodies. Human embryonic stem cells are expected for use as resources for cell transplantation therapies for various diseases such as Parkinson's disease, juvenile diabetes, and leukemia, taking advantage of the aforementioned properties. However, transplantation of ES cells has a problem of causing rejection in the same manner as organ transplantation. Moreover, from an ethical viewpoint, there are many dissenting opinions against the use of ES cells which are established by destroying human embryos.

If dedifferentiation of patients' own differentiated somatic cells could be induced to establish cells having pluripotency and growth ability similar to those of ES cells (these cells are referred herein to as "induced pluripotent stem cells" or "iPS cells," though they are sometimes called "embryonic stem cell-like cells" or "ES-like cells"), it is expected that such cells would be useful as ideal pluripotent cells, free from rejection or ethical difficulties. Recently, it has been reported that such iPS cells can be produced from differentiated cells of mouse or human, which has created a great sensation (International Publication No. WO2007/069666 A1; Takahashi et al., Cell 126:663-76, 2006; Takahashi et al., Cell 131:861-72, 2007; Yu et al., Science 318:1917-20, 2007; and Park et al., Nature 451:141-46, 2008, herein incorporated by reference in their entireties). Thus, the term "induced pluripotent stem cells (iPS cells)" refers to cells having similar properties to those of ES cells, and more specifically the term includes undifferentiated cells which are reprogrammed from somatic cells and have pluripotency and proliferation potency. However, this term is not to be construed as limiting in any sense, and should be construed to have its broadest meaning.

These methods include a reprogramming step through introduction of a plurality of specific factors (for example, four factors of Oct3/4, Sox2, Klf4, and c-Myc can be used in Takahashi et al., Cell 126:663-76, 2006), and the introduction of these factors is mediated by viral vectors such as retroviral or lentiviral vectors. However, all previously reported nuclear reprogramming methods mediated by the introduction of genes involve a problem of low efficiency in which only a small number of induced pluripotent stem cells can be obtained. In particular, there is a problem in that, if reprogramming is carried out in somatic cells through the introduction of three factors (namely, Oct3/4, Sox2, and Klf4) excluding c-Myc, then the production efficiency of induced pluripotent stem cells becomes low. Nevertheless, the efficient production of iPS cells without the use of c-Myc would provide certain advantages, as c-Myc is suspected to cause tumorigenesis in tissues and in chimeric mice generated from induced pluripotent stem cells.

It is known that various small RNAs are expressed in cells. Examples of small RNA include RNA molecules of about 18-25 nucleotides in length which can be cleaved out with a dicer, an RNase specific to double-stranded RNA. Small RNA is mainly classified into siRNA (small interfering RNA) and miRNA (microRNA, hereinafter abbreviated as "miRNA"). Small RNA is known to function as a guide molecule for finding target sequences in processes such as translational suppression, mRNA degradation, or alteration of chromatin structure. Small RNAs function via RNA interference (RNAi) or miRNA molecular mechanisms. In addition, small RNA is also known to play an important role in the regulation of developmental processes (for example, as general remarks, refer to Jikken Igaku (Experimental Medicine), 24, pp. 814-819, 2006; and microRNA Jikken Purotokoru (microRNA Experimental Protocol), pp. 20-35, 2008, YODOSHA CO., LTD., herein incorporated by reference in their entireties).

ES cell-specific microRNAs have been identified (Houbaviy et al., Developmental Cell 5:351-58, 2003). In particular, ES cell-specific expression of a microRNA cluster, which includes several types of miRNAs in mouse ES cells, has been reported (Houbaviy et al., Developmental Cell 5:351-58, 2003, herein incorporated by reference in its entirety). It has also been reported that miRNA-295 suppressed the expression of Rbl2, a member of the Rb tumor suppressor gene family, and increased the expression of methylase to be thereby associated with DNA methylation (Sinkkonen et al., Nature Structural & Molecular Biology 15:259-267, 2008; Benetti et. al., Nature Structural & Molecular Biology 15:268-279, 2008, herein incorporated by reference in their entireties). However, these documents do not disclose any role of small RNA in the nuclear reprogramming of somatic cells.

SUMMARY OF THE INVENTION

The present invention relates to methods for efficiently preparing induced pluripotent stem cells. The present invention provides methods for achieving efficient preparation of induced pluripotent stem cells in the presence of miRNA. The present invention also provides methods for efficient preparation of induced pluripotent stem cells with a nuclear reprogramming factor. The present invention also provides methods for efficient preparation of induced pluripotent stem cells with a nuclear reprogramming factor in the presence of increased miRNA as compared to the level present in the somatic cell prior to nuclear reprogramming. The present invention also provides such methods wherein the nuclear reprogramming factor does not include c-Myc and/or Sox2.

The invention provides a method of preparing induced pluripotent stem cells, comprising nuclear reprogramming at least one somatic cell with nuclear reprogramming factor and at least one miRNA, wherein the at least one miRNA increases efficiency of the nuclear reprogramming of the at least one somatic cell compared to nuclear reprogramming of the at least one somatic cell with the nuclear reprogramming factor in the absence of the at least one miRNA.

The invention also provides such a method, wherein the at least one miRNA is expressed in embryonic stem cells at a higher level than in somatic cells.

The invention also provides such a method, wherein a gene encoding the nuclear reprogramming factor and/or the at least one miRNA is introduced into the at least one somatic cell.

The invention also provides such a method, wherein a vector comprising the gene and/or a vector encoding the at least one miRNA is introduced into the at least one somatic cell.

The invention also provides such a method, wherein the vector comprising the gene or encoding the at least one miRNA is a retroviral vector.

The invention also provides such a method, wherein the gene is selected from an Oct family gene, a Klf family gene, and a Sox family gene.

The invention also provides such a method, wherein the gene is selected from Oct3/4, Klf4, and Sox2.

The invention also provides such a method, wherein the nuclear reprogramming factor comprises Oct3/4, Klf4, and Sox2.

The invention also provides such a method, wherein the at least one miRNA is introduced into the at least one somatic cell as primary miRNA.

The invention also provides such a method, wherein the at least one miRNA is introduced into the at least one somatic cell as pre-miRNA.

The invention also provides such a method, wherein the at least one miRNA comprises at least one miRNA represented by SEQ ID NOs: 1 to 14.

The invention also provides such a method, wherein the at least one miRNA comprises at least one miRNA contained in miRNA cluster hsa-miR-302-367 cluster.

The invention also provides such a method, wherein the at least one miRNA regulates DNA methylation.

The invention also provides such a method, wherein the at least one miRNA regulates de novo DNA methylation.

The invention also provides such a method, wherein the at least one miRNA down-regulates DNA methylation.

The invention also provides such a method, wherein the at least one miRNA comprises at least 10 contiguous nucleotides of at least one miRNA represented by SEQ ID NOs: 1 to 14.

The invention also provides such a method, wherein the at least one miRNA comprises at least 30 contiguous nucleotides of at least one miRNA represented by SEQ ID NOs: 1 to 14.

The invention also provides such a method, wherein the at least one miRNA comprises at least 60 contiguous nucleotides of at least one miRNA represented by SEQ ID NOs: 1 to 14.

The invention also provides such a method, wherein the nuclear reprogramming factor does not include c-Myc and/or Sox2.

The invention also provides such a method, wherein the at least one miRNA comprises hsa-miR-302-367 cluster miRNA.

The invention also provides such a method, wherein the nuclear reprogramming factor comprises an Oct family gene member, a Sox family gene member, and a Klf family gene member.

The invention also provides such a method, wherein the at least one miRNA comprises mmu-miR-295/295* and mmu-miR-294/294*.

The invention also provides such a method, wherein the at least one miRNA comprises hsa-miR-302-367 cluster, hsa-miR-371-373 cluster and hsa-miR-520c miRNA.

The invention also provides such a method, wherein the nuclear reprogramming factor comprises a Klf family gene, and an Oct family gene.

The invention also provides such a method, wherein the nuclear reprogramming factor further comprises a Myc family gene.

The invention also provides such a method, wherein the nuclear reprogramming factor further comprises a Sox family gene.

The invention also provides such a method, wherein the nuclear reprogramming factor further comprises a Sox family gene.

The invention also provides such a method, wherein the nuclear reprogramming factor comprises KLF4 and OCT3/4.

The invention also provides such a method, wherein the nuclear reprogramming factor excludes a Sox family gene.

The invention also provides such a method, wherein the nuclear reprogramming factor excludes a Myc family gene.

The invention also provides such a method, where the at least one somatic cell comprises a plurality of somatic cells.

The invention also provides a method of increasing the efficiency of nuclear reprogramming comprising: adding a nuclear reprogramming factor and at least one miRNA to at least one somatic cell so that the number of induced pluripotent stem cells produced is greater than in the absence of the added miRNA.

The invention also provides an induced pluripotent stem cell induced by reprogramming a somatic cell, wherein the reprogramming is performed by adding at least one miRNA and in the absence of eggs, embryos, or embryonic stem (ES) cells.

The invention also provides such an induced pluripotent stem cell, wherein the induced pluripotent stem cell is a human cell.

The invention also provides an induced pluripotent stem cell obtained by a method of preparing induced pluripotent stem cells, comprising nuclear reprogramming at least one somatic cell with nuclear reprogramming factor and at least one miRNA, wherein the at least one miRNA increases efficiency of the nuclear reprogramming of the at least one somatic cell compared to nuclear reprogramming of the at least one somatic cell with the nuclear reprogramming factor in the absence of the at least one miRNA.

The invention also provides an pluripotent stem cell obtained by a method of increasing the efficiency of nuclear reprogramming comprising: adding a nuclear reprogramming factor and at least one miRNA to at least one somatic cell so that the number of induced pluripotent stem cells produced is greater than in the absence of the added miRNA.

The invention also provides somatic cell derived by inducing differentiation of any of the above pluripotent stem cells.

The present invention further provides a method of preparing an induced pluripotent stem cell from a somatic cell, comprising nuclear reprogramming the somatic cell with at least one nuclear reprogramming factor and at least one miRNA, wherein the at least one miRNA increases efficiency of the nuclear reprogramming of the somatic cell compared to nuclear reprogramming of the somatic cell with the at least one nuclear reprogramming factor in the absence of the at least one miRNA, and wherein the at least one nuclear reprogramming factor comprises at least (i) an Oct family gene, (ii) an Oct family gene and a Klf family gene, (iii) an Oct family gene and a Nanog gene, or (iv) an Oct family gene, Klf family gene, and a Myc family gene, but it does not comprise a Sox family gene.

The present invention yet further provides a method of increasing the efficiency of nuclear reprogramming for inducing an induced pluripotent stem cell from a somatic cell, comprising subjecting the somatic cell to nuclear reprogramming with at least one nuclear reprogramming factor in the presence of at least one miRNA, so that the number of induced pluripotent stem cells produced is greater than in the absence of the miRNA, wherein the at least one miRNA increases efficiency of the nuclear reprogramming of the somatic cell compared to nuclear reprogramming of the somatic cell with the at least one nuclear reprogramming factor in the absence of the at least one miRNA, and wherein the at least one nuclear reprogramming factor comprises at least (i) an Oct family gene, (ii) an Oct family gene and a Klf family gene, (iii) an Oct family gene and a Nanog gene, or (iv) an Oct family gene, Klf family gene, and a Myc family gene, but it does not comprise a Sox family gene.

The invention also provides each of such methods, wherein the at least one miRNA is expressed in embryonic stem cells at a higher level than in somatic cells.

The invention also provides each of such methods, wherein the Oct family gene is an Oct3/4 gene, the Klf family gene is a Klf4 gene, the Myc family gene is a c-Myc gene, or the Sox family gene is a Sox2 gene.

The invention also provides each of such methods, wherein the at least one nuclear reprogramming factor is (i) a Oct3/4 gene, (ii) a combination of an Oct3/4 gene and a Klf4 gene, (iii) a combination of an Oct3/4 gene and a Nonog gene, or (iv) a combination of an Oct3/4 gene, a Klf4 gene and a c-Myc gene.

The invention also provides each of such methods, wherein the at least one nuclear reprogramming factor is introduced in the form of a vector comprising DNA encoding the nuclear reprogramming factor, into the somatic cell.

The invention also provides each of such methods, wherein the at least one miRNA is introduced in the form of a vector comprising DNA encoding the miRNA or a precursor RNA thereof, into the somatic cell.

The invention also provides each of such methods, wherein the at least one miRNA is one or two or more miRNAs contained in one or two or more RNAs selected from the group consisting of: hsa-miR-372; hsa-miR-373 or hsa-miR-373/373*; hsa-miR-371-373 cluster; hsa-miR-302b or hsa-miR-302b/302b*; hsa-miR-302-367 cluster; hsa-miR-520c or hsa-miR-520c-5p/520c-3p; mmu-miR-291a or mmu-miR-291a-5p/291a-3p; mmu-miR-294 or mmu-miR-294/294*; and mmu-miR-295 or mmu-miR-295/295*, where the symbols represent accession numbers from the miRBase database.

The invention also provides each of such methods, wherein the at least one miRNA is one or two or more miRNAs contained in one or two or more RNAs selected from the group consisting of RNAs represented by SEQ ID NOS:1 to 5, 10 to 12, and 14.

The invention also provides each of such methods, wherein the at least one miRNA is 18-25 nucleotides in length.

The invention also provides each of such methods, wherein the somatic cell is of a human.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows the number of human ES-like colonies obtained induced by transduction with 4 factors (OSMK), and with 3 factors without c-MYC plus miRNAs (OSK+). FIG. 4B shows the morphology of ES-like colonies from a subset of the samples counted in FIG. 4A.

FIGS. 6A-B show the results of MEFs infected with 3 factors (Oct3/4, c-MycWT, and Klf4, i.e., "Sox(−)") with mmu-miR-290-295 cluster, 290-5p/290-3p(mmu-miR-290), 291a-5p/291a-3p(mmu-miR-291a), 292-5p/292-3p(mmu-miR-292), 293/293*(mmu-miR-293), 294/294*(mmu-miR-294) or 295/295*(mmu-miR-295). FIG. 6A shows the number of Nanog GFP positive colonies. FIG. 6B shows expression of ES marker genes in iPS cells checked with RT-PCR.

FIGS. 7A-C show the results of iPS induction with Fb-Ng MEFs (MEFs derived from Fbx15-β geo/Nanog-IRES-Puro[r] reporter mouse) over-expressing Oct3/4, c-Myc, and Klf4 ("Sox(−)")+mmu-miR-295/295* or hsa-miR-302-367 cluster miRNAs. FIG. 7A shows cell morphology of MEFs transduced with Oct3/4, c-Myc, and Klf4 ("Sox(−)")+mmu-miR-295/295*. FIG. 7B shows chimeras derived from iPS cells induced with Sox(−)3f+mmu-miR-295/295*. FIG. 7C shows embryoid body (EB)-mediated in vitro differentiation by human iPS cells. Human iPS cells (61B1, 61N2) were established by transduction of 4 genes (OCT3/4, KLF4, SOX2, and c-MYC, i.e., "OSMK") or 3 genes (OCT3/4, KLF4, and c-MYC, i.e., "OMK(SOX(−)") in the presence of hsa-miR-302-367 cluster miRNA. After culturing for 16 days, immunohistochemistry analysis was performed in the cells by using an antibody against each of α-fetoprotein (AFP) which is a differentiation marker for endodermal cells, α-smooth muscle actin (a-SMA) which is a differentiation marker for mesodermal cells, and GFAP (DAKO) which is a differentiation marker for ectodermal cells. Nuclei were stained with Hoechst 33342 (Invitrogen).

FIG. 8 shows cell morphology of iPS cells induced with OSMK (61B1); SOX(−)(OKM)+hsa-miR-302-367 cluster miRNA (61N2); and OCT3/4+KLF4+hsa-miR-302-367 cluster miRNA (133O1) (FIG. 8A), and also shows that the iPS cells (133O1) are positive for alkaline phosphatase, i.e., red-stained (FIG. 8B).

In FIG. 14, "O+h-mir-302 cluster" indicates iPS cell clones established by introducing OCT3/4 and hsa-mir-302-367 cluster miRNA. "133O1" indicates iPS cell clones established by introducing OCT3/4, KLF4 and hsa-mir-302-367 cluster miRNA. "61N2" indicates iPS cell clones established by introducing OCT3/4, c-MYC, KLF4 and hsa-mir-302-367 cluster miRNA. "168C1" indicates iPS cell clones established by introducing OCT3/4, SOX2 and KLF4. "201B7" indicates iPS cell clones established by introducing OCT3/4, SOX2, c-MYC and KLF4. "aHDF-Slc7a1" indicates adult human dermal fibroblast expressing Slc7a1.

In FIG. 15, "O+h-mir-302 cluster" indicates iPS cell clones established by introducing OCT3/4 and hsa-miR-302-367 cluster miRNA. "133O1" indicates iPS cell clones established by introducing OCT3/4, KLF4 and hsa-miR-302-367 cluster miRNA. "61N2" indicates iPS cell clones established by introducing OCT3/4, c-MYC, KLF4 and hsa-miR-302-367 cluster miRNA. "168C1" indicates iPS cell clones established by introducing OCT3/4, SOX2 and KLF4. "201B7" indicates iPS cell clones established by introducing OCT3/4, SOX2, c-MYC and KLF4. "hES" indicates human ES cells. "aHDF-Slc7a1" indicates adult human dermal fibroblast expressing Slc7a1.

Figure 1:
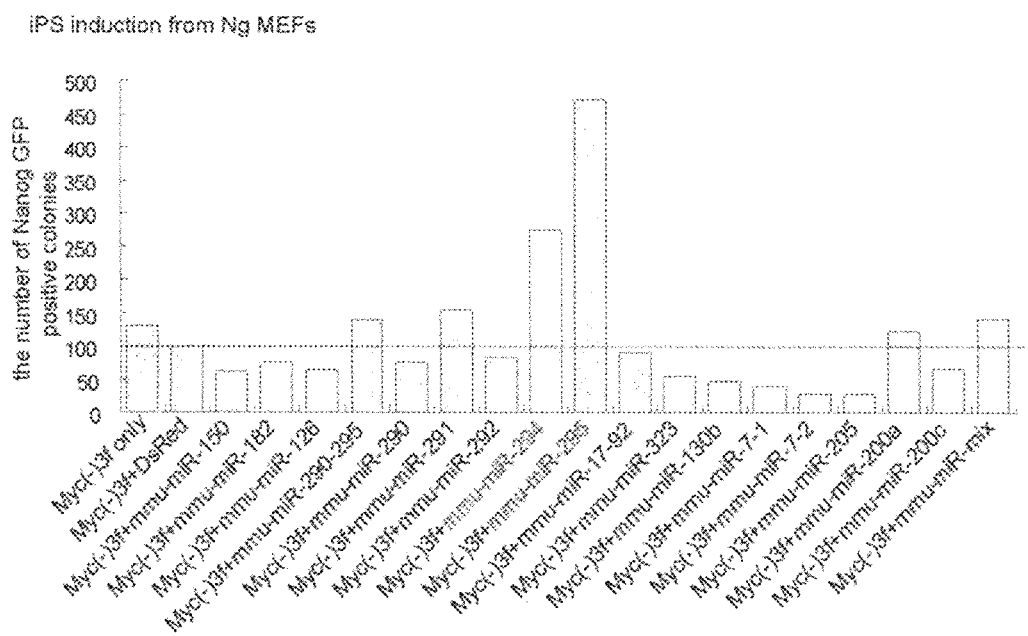
FIG. 1 shows the results of confirmation on the production efficiency of induced pluripotent stem cells through induction of nuclear reprogramming in mouse embryonic fibroblasts with a combination of three genes comprising Oct3/4, Klf4, and Sox2 (this combination—represented as "3f", "c-Myc(−)", or OSK"—means that c-Myc was omitted from a combination of four genes comprising Oct3/4, Klf4, Sox2 and c-Myc, which is highly efficient for nuclear reprogramming), in the presence of various miRNAs. 3f+DsRed represents a combination where DsRed (*Discosoma* sp. red fluorescent protein) as a control was added to the combination of the aforementioned three genes. The results of three independent experiments are shown. The graph shows the number of ES-like colonies in the cells transduced with OSK with or without DsRed, or with various miRNAs.

TABLE 3 shows iPS induction by transduction with 4 factors (OCT3/4, SOX2, MYC, KLF4, i.e., "OSMK"), with 3 factors (SOX(−)3 factors, i.e., "OMK") plus various miRNAs (OMK:mock or miRNAs=2.5:1.5), and with 2 factors (OCT3/4+KLF4, i.e., "OK") plus various miRNAs. Transduction with DsRed was performed as a control. On Day 40 after infection, the number of ES-like colonies was counted. TABLE 3 shows the results of six independent experiments (Exp. 54, 61, 63, 114, 130 and 133).

DETAILED DESCRIPTION OF THE INVENTION

The present invention provides methods for efficiently preparing induced pluripotent stem cells through reprogramming of one or more somatic cells. In particular, the present invention provides efficient preparation of induced pluripotent stem cells in the presence of miRNA. The present invention also provides efficient preparation with or without using a suspected tumorigenic factor: c-Myc. The present invention also provides efficient preparation with or without using Sox2. The nuclear reprogramming is preferably performed without c-Myc and/or Sox2.

The inventors of the present invention have conducted intensive studies, and as a result, they have found that induced pluripotent stem cells can be efficiently prepared by introduction of nuclear reprogramming-inducing gene(s) into somatic cells in the presence of specific miRNA. The present invention was achieved on the basis of the above findings.

The present invention thus provides a method of preparing induced pluripotent stem cells, comprising nuclear reprogramming with a nuclear reprogramming factor in the presence of miRNA, wherein said miRNA has a property of providing a higher nuclear reprogramming efficiency in the presence of said miRNA than in the absence thereof.

A preferred embodiment of the present invention provides the aforementioned method wherein: (a) said miRNA is expressed in embryonic stem cells at a higher level than in somatic cells; and/or (b) said miRNA has a property of providing a higher nuclear reprogramming efficiency in the presence of said miRNA than in the absence thereof and/or (c) said nuclear reprogramming is performed in the presence of increased levels of one or more miRNAs as compared to the level(s) present in the somatic cell prior to nuclear reprogramming.

Another preferred embodiment of the present invention provides: the aforementioned method wherein the nuclear reprogramming factor is either a single substance, or a combination of a plurality of substances, which is/are positive in the screening method of nuclear reprogramming factor described in International Publication No. WO2005/80598 A1, incorporated by reference herein in its entirety; the aforementioned method wherein the nuclear reprogramming factor is either a gene product of a single gene, or a combination of gene products of a plurality of genes, which is/are positive in the screening method of nuclear reprogramming factor described in International Publication No. WO2005/80598 A1, incorporated by reference herein in its entirety; the aforementioned method wherein the nuclear reprogramming with the nuclear reprogramming factor is carried out by introduction of the aforementioned gene(s) and/or substance(s) into somatic cells; the aforementioned method wherein introduction of the aforementioned gene(s) into somatic cells is carried out with a recombinant vector; and the aforementioned method wherein the nuclear reprogramming with the nuclear reprogramming factor is carried out by introduction of gene product(s) of the aforementioned gene(s) into somatic cells.

Yet another preferred embodiment of the present invention provides the aforementioned method wherein: the gene encoding the reprogramming factor comprises one or more gene(s) selected from an Oct family gene, a Klf family gene, a Sox family gene, a Myc family gene, a Lin family gene, and a Nanog gene, preferably a combination of two genes selected from the aforementioned genes except for the Myc family genes of Sox family genes, more preferably a combination of three genes, and particularly preferably a combination four or more genes. In a preferred embodiment, the combination can be any combination of factors which does not comprise c-Myc or Sox2.

More preferable combinations are: (a) a combination of two genes comprising of an Oct family gene and a Sox family gene; (b) a combination of three genes comprising an Oct family gene, a Klf family gene, and a Sox family gene; and (c) a combination of four genes comprising an Oct family gene, a Sox family gene, a Lin family gene, and a Nanog gene. Further, it is also preferable to combine any of the above genes with a TERT gene and/or a SV40 Large T antigen gene. It may be preferable to omit Klf family genes depending on the situation. The Myc family genes may or may not be included in these combinations. Combinations without the Myc family gene can be suitably used according to the present invention.

Among these embodiments, particularly preferable combinations are: a combination of two genes comprising Oct3/4 and Sox2; a combination of three genes comprising Oct3/4, Klf4, and Sox2; and a combination of four genes comprising Oct3/4, Sox2, Lin28, and Nanog. It is also preferable to combine any of the above genes with a TERT gene and/or a SV40 Large T antigen gene. It may be preferable to omit Klf4 depending on the situation. c-Myc may be included in these combinations. However, combinations without c-Myc can be suitably used in the present invention.

Other preferable combinations are: (a) a combination of two genes comprising an Oct family gene and a Klf family gene; (b) a combination of two genes comprising an Oct family gene and Nanog gene; and (c) a combination of three genes comprising an Oct family gene, a Klf family gene and a Myc family gene.

It is possible to employ an Oct family gene alone as the nuclear reprogramming factor.

For the nuclear reprogramming factors as mentioned above, preferably the Oct family gene is an Oct3/4 gene, the Klf family gene is a Klf4 gene, the Myc family gene is a c-Myc gene, and the Sox family gene is a Sox2 gene.

Other examples of the nuclear reprogramming factors preferred in the invention are: (i) an Oct3/4 gene, (ii) a combination of an Oct3/4 gene and a Klf4 gene, (iii) a combination of an Oct3/4 gene and a Nonog gene, or (iv) a combination of an Oct3/4 gene, a Klf4 gene and a c-Myc gene.

Yet another preferred embodiment of the present invention provides: the aforementioned method wherein the somatic cells are those derived from mammals, such as primates, rodents, ungulates, and pet animals, including for example human, mouse, rat, cattle, sheep, horse, monkey, dog, cat, and hamster, preferably somatic cells from human or mouse, and most preferably somatic cells from human. The somatic cells as used herein refer to any cells other than germ cells, germline cells or germate-derived cells, such as eggs or oocytes, sperm cells or spermatocytes, and embryonic stem cells. Examples of the somatic cells include all tissue-derived cells, hematopoietic cells, lymphoid cells or lymphocytes, tissue stem cells (i.e., somatic stem cells), etc. Also, the somatic cells are from matured or inmatured individuals, who may be healthy or normal or may have a disease(s), such as adults, embryos, fetuses, neonates, etc., preferably from healthy humans or human patients.

Yet another preferred embodiment of the present invention provides the aforementioned method wherein the miRNA comprises one or more miRNA(s) included in the RNA sequences specified by the registration names of the miRBase database or the accession numbers shown in Table 1 or Table 2; the aforementioned method wherein the RNA sequences specified by the registration names of the miRBase database (and the accession numbers) shown in Table 1 or Table 2 comprise one or two or more RNA(s) selected from hsa-miR-372 (MI0000780), hsa-miR-373 (MI0000781), hsa-miR-302b (MI0000772), hsa-miR-302c (MI0000773), hsa-miR-302a (MI0000738), hsa-miR-302d (MI0000774), hsa-miR-367 (MI0000775), hsa-miR-520c (MI0003158), mmu-miR-290 (MI0000388), mmu-miR-291a (MI0000389), mmu-miR-294 (MI0000392), and mmu-miR-295 (MI0000393); the aforementioned method wherein the miRNA comprises miRNA included in RNA specified by hsa-miR-302-367; and the aforementioned method wherein the miRNA comprises one or two or more miRNAs included in one or two or more RNA sequences selected from the RNA sequences represented by SEQ IDS:1 to 14, preferably SEQ ID NOS:1 to 5, 10 to 12 and 14, in the Sequence Listing. In the above-described registration names, the symbols "hsa" and "mmu" represent *Homo sapiens* and *Mus musculus*, respectively.

The present invention provides an oligonucleotide comprising at least 10 contiguous nucleotides in the nucleotide sequence of the miRNA of the present invention, and an antisense oligonucleotide having a sequence that is complementary to that of the above oligonucleotide. The present invention also provides an oligonucleotide comprising at least 15, at least 20, at least 30, at least 50, or at least 60 contiguous nucleotides in the nucleotide sequence of the miRNA of the present invention. The present invention also provides an oligonucleotide comprising at least 70, at least 80, at least 100, at least 150, at least 200, at least 300, at least 400, at least 600, or at least 800 contiguous nucleotides in the nucleotide sequence of the miRNA of the present invention.

In a preferred embodiment, the size of an active miRNA is normally 18-25 nucleotides, preferably 20-25 nucleotides, more preferably 21-23 nucleotides. Such active miRNAs can be induced from precursor RNAs including pri-miRNAs (i.e., transcription products from genomic DNAs) and pre-miRNAs (i.e., processed products from pri-miRNAs).

The present invention also provides induced pluripotent stem cells that can be obtained by the aforementioned method. In addition, the present invention also provides somatic cells obtained by inducing differentiation from the abovementioned induced pluripotent stem cells.

Further, the present invention provides a stem cell therapy comprising transplanting somatic cells into a patient, wherein the somatic cells are obtained by inducing differentiation from induced pluripotent stem cells that are obtained according to the aforementioned method by using somatic cells isolated and collected from a patient.

In addition, the present invention provides a method for evaluation of physiological effect or toxicity of a compound, a drug, or a toxic agent, with use of various cells obtained by inducing differentiation from induced pluripotent stem cells that are obtained by the aforementioned method.

Further, the present invention provides: a method for preparing induced pluripotent stem cells which uses miRNA expressed in embryonic stem cells at a higher level than in somatic cells, and having a property of providing a higher nuclear reprogramming efficiency in the presence of said miRNA than in the absence thereof; and a nuclear reprogramming method of somatic cells which uses miRNA expressed in embryonic stem cells at a higher level than in somatic cells, and having a property of providing a higher nuclear reprogramming efficiency in the presence of said miRNA than in the absence thereof.

In addition, the present invention provides methods comprising the use of miRNA expressed in embryonic stem cells at a higher level than in somatic cells (e.g., the miRNA may be expressed at levels which are higher in the ES cell as compared to the ES cell which has differentiated or which has begun differentiating such as determined by RT-PCR or Northern blot analysis), and having a property of providing a higher nuclear reprogramming efficiency in the presence of said miRNA than in the absence thereof, for preparation of induced pluripotent stem cells; and methods relating to the use of miRNA expressed in embryonic stem cells at a higher level than in somatic cells, and having a property of providing a higher nuclear reprogramming efficiency in the presence of the miRNA than in the absence thereof, for nuclear reprogramming of somatic cells. In other words, nuclear reprogramming, and thus, induced pluripotent stem cell production, can be performed in the presence of miRNA and in the absence of miRNA. The nuclear reprogramming may also be performed in the presence of various amounts and/or kinds of miRNA, such that, for example, the efficiency of the nuclear reprogramming is increased when the level of the miRNA is increased in the somatic cell prior to nuclear reprogramming.

In addition, the present invention provides methods comprising the use of miRNA having a property of providing a higher nuclear reprogramming efficiency in the presence of said miRNA than in the absence thereof, for preparation of induced pluripotent stem cells. For example, the presence of added miRNA can provide the formation of an induced pluripotent stem cell as compared to the lack of formation in the absence of the miRNA. Also, for example when nuclear reprogramming is performed on the same number of somatic cells in the presence of a nuclear reprogramming factor containing the same components in the same concentrations with and without addition of miRNA, increased efficiency can be observed when a greater number of induced pluripotent stem cells are generated in the sample which comprises the addition of miRNA than in the sample without the addition of miRNA. In another embodiment, increased efficiency of induced pluripotent stems cell production can also be achieved with increased amounts of miRNA as compared to miRNA amounts present in the somatic cell prior to nuclear reprogramming.

According to the present invention, the term "higher nuclear reprogramming efficiency" as used herein means that the number of induced pluripotent stem (iPS) cells generated in the presence of miRNA(s) is greater than that of iPS cells generated in the absence of miRNA(s), for example, with a difference of about 1.1 fold or greater, about 1.2 fold or greater, about 1.3 fold or greater, or about 1.4 fold or greater, preferably about 1.5 fold or greater, about 1.7 fold or greater, about 2 fold or greater, about 2.3 fold or greater, about 2.5 fold or greater, or about 2.7 fold or greater, more preferably about 3 fold or greater, about 4 fold or greater, about 5 fold or greater, about 6 fold or greater, about 7 fold or greater, or about 10 fold or greater. This difference is statistically significant with $p<0.05$, preferably $p<0.01$.

Gene names of nuclear reprogramming factors as used herein are represented by murine gene names of Oct, Nanog, Sox, Klf, Myc, Lin, etc., unless otherwise indicated. These gene names are used herein not only in case of mouse-derived genes but also in case of genes from the other mammals including human.

BEST MODE FOR CARRYING OUT THE INVENTION

The methods of the present invention relate to, e.g., a method for preparing induced pluripotent stem cells, comprising nuclear reprogramming with a nuclear reprogramming factor in the presence of miRNA, wherein said miRNA has a property of providing a higher nuclear reprogramming efficiency in the presence of said miRNA than in the absence thereof. In a preferred embodiment of the present invention, (a) said miRNA is expressed in embryonic stem cells at a higher level than in somatic cells; and (b) said RNA has a property of providing a higher nuclear reprogramming efficiency in the presence of said miRNA than in the absence thereof.

As for the miRNA, for example, its classification and in vivo functions are described in *Jikken Igaku* (Experimental Medicine), 24, pp. 814-819, 2006; microRNA *Jikken Purotokoru* (microRNA Experimental Protocol), pp. 20-35, 2008, YODOSHA CO., LTD. The number of nucleotides of miRNA is for example 18 to 25, and preferably about 19 to 23. At present, a database storing data relating to about 1,000 miRNA sequences is available (for example, miRBase, Griffiths-Jones et al. *Nucleic Acids Research* 36:D154-D158, 2008 (published online Nov. 8, 2007), see also http://microma.sanger.ac.uk/sequences/index.shtml [on-line]), and it is possible for those skilled in the art to obtain any miRNA data therefrom, and to readily extract miRNA expressed in embryonic stem cells at a higher level than in somatic cells. In addition, it is also possible to readily specify miRNA expressed in embryonic stem cells at a higher level than in somatic cells by confirming the difference in miRNA expression between embryonic stem cells and somatic cells with use of available techniques for those skilled in the art such as miRNA microarray and real-time PCR analyses.

The difference in the nuclear reprogramming efficiency with and without miRNA can be understood by the following manner, as specifically described in Examples of this application: transgenic mice are generated by insertion of sequences encoding Enhanced Green Fluorescent Protein (EGFP) and a puromycin resistance gene downstream of a Nanog gene promoter region, the expression of which is specific to ES cells; then, one, two or three genes as described above (for example, Oct3/4, Sox2 and Klf4 genes) and different miRNAs are introduced into embryonic fibroblasts from these transgenic mice to induce nuclear reprogramming, followed by confirmation of the production efficiency of induced pluripotent stem cells. The genes, the miRNAs, and both thereof may be introduced into the somatic cells in the form of at least one vector comprising DNAs encoding the gene(s) and/or the miRNA(s). The production efficiency can be determined, for example, by counting the number of colonies. More specifically, the number of colonies can be compared by the following manner: drug selection is started from about the 21st day after introduction of the above genes and miRNA; and the number of total colonies and the number of Nanog GFP positive colonies (GFP, the expression of which is induced by the Nanog gene promoter region, is observable under fluorescent microscopy) are counted on about the 28th day. It should be understood, however, that: the confirmation of the nuclear reprogramming efficiency is not limited to the above method; appropriate modification and alteration can be made in the above method; and any appropriate method can be employed by those skilled in the art.

As for the miRNA, it is preferable to use miRNA derived from the same animal species as the target animal whose somatic cells are to be reprogrammed. Usable miRNA includes wild type miRNA as well as miRNAs in which one to several nucleotides (for example 1 to 6 nucleotides, preferably 1 to 4 nucleotides, more preferably 1 to 3 nucleotides, yet more preferably 1 or 2 nucleotides, and most preferably 1 nucleotide) are substituted, inserted, and/or deleted, and which are capable of exerting equivalent functions to those of the wild type miRNA in vivo. For example, the miRNA of the present invention includes miRNAs in which one to several nucleotides are substituted, inserted, and/or deleted, and which increase the efficiency of iPS cell production. The miRNA of the present invention also includes miRNAs in which one to several nucleotides are substituted, inserted, and/or deleted, and which improve the efficiency of nuclear reprogramming. The miRNA of the present invention also includes miRNAs in which one to several nucleotides are substituted, inserted, and/or deleted, and which regulate DNA methylation. The present invention also includes such miRNAs wherein the DNA methylation is down-regulated. The present invention also includes such miRNAs wherein the DNA methylation is de novo DNA methylation.

Examples of the miRNA preferably used in the methods of the present invention can include, but are not limited to, one or more miRNA(s) included in the following RNA sequences registered in the miRBase: hsa-miR-372 (MI0000780), hsa-miR-373 (MI0000781), hsa-miR-302b (MI0000772), hsa-miR-302c (MI0000773), hsa-miR-302a (MI0000738), hsa-miR-302d (MI0000774), hsa-miR-367 (MI0000775), hsa-miR-520c (MI0003158), mmu-miR-290 (MI0000388), mmu-miR-291a (MI0000389), mmu-miR-294 (MI0000392), and mmu-miR-295 (MI0000393)(Numbers in the brackets respectively indicate miRBase accession numbers. The symbol "hsa-miR-" represents human miRNA, and the symbol "mmu-miR-" represents mouse miRNA.).

In the method of the present invention, miRNAs that have been confirmed to improve the nuclear reprogramming efficiency in the above manner can be used either alone or in combinations of two or more types. In addition, a plurality of miRNAs forming a cluster may also be used. For example, hsa-miR-302-367 which is available as a miRNA cluster, or individual miRNAs from the hsa-miR-302-367 cluster, and the like may be used. Examples of RNA sequences for use in the present invention are shown in SEQ IDS: 1 to 14 in the Sequence Listing. SEQ ID: 1: mmu-miR-294 (MI0000392); SEQ ID: 2: mmu-miR-295 (MI0000393); SEQ ID: 3: hsa-miR-372 (MI0000780); SEQ ID: 4: hsa-miR-373 (MI0000781); SEQ ID: 5: hsa-miR-302b (MI0000772); SEQ ID: 6: hsa-miR-302c (MI0000773); SEQ ID: 7: hsa-miR-302a (MI0000738); SEQ ID: 8: hsa-miR-302d (MI0000774); SEQ ID: 9: hsa-miR-367 (MI0000775); SEQ ID: 10: hsa-miR-520c (MI0003158); SEQ ID: 11: mmu-miR-291a (MI0000389); SEQ ID:13: mmu-miR-290 (MI0000388), and SEQ ID:14: hsa-miR-371-373 cluster. In addition, RNA represented by SEQ ID: 12: hsa-miR-302-367 cluster can also be preferably used. Among these RNA sequences, some RNA sequences may include a plurality of miRNAs within one sequence. Use of such an RNA sequence may achieve efficient production of iPS cells. Further, an RNA sequence including a plurality of miRNAs within one sequence and one or more other RNA sequence(s) including one or more miRNA(s) can also be used in combination. In the invention, preferably, the miRNAs are one or two or more miRNAs contained in one or two or more RNAs selected from RNAs represented by SEQ ID NOS:1 to 5, 10 to 12 and 14.

miRNA is non-coding RNA which is not translated into a protein. miRNA is first transcribed as pri-miRNA from a corresponding gene, then this pri-miRNA generates pre-miRNA having a characteristic hairpin structure of about 60 to about 120 nucleotides or more, for example about 70 nucleotides, and this pre-miRNA is further processed into mature miRNA, which is mediated by Dicer. In the present invention, not only mature miRNA but also precursor RNA thereof (i.e., pri-miRNA or pre-miRNA), or a vector comprising DNA encoding the miRNA or precursor RNA, can be used as long as the effect of the present invention is not impaired. In addition, miRNA for use in the present invention may be either natural type or non-natural type. Thus, any small RNA or RNA precursor may be used as long as the effect of the present invention is not impaired.

The production method of miRNA for use in the present invention is not specifically limited, although the production can be achieved, for example, by a chemical synthetic method or a method using genetic recombination technique.

When the production is carried out by a method using genetic recombination technique, miRNA for use in the present invention can, for example, be produced through transcription reaction with use of a DNA template and a RNA polymerase obtained by means of gene recombination. Examples of usable RNA polymerase include a T7 RNA polymerase, a T3 RNA polymerase, and a SP6 RNA polymerase.

Alternatively, a recombinant vector capable of expressing miRNA can be produced by insertion of miRNA-encoding DNA or precursor RNA (pri-miRNA or pre-miRNA)-encoding DNA into an appropriate vector under the regulation of expression control sequences (promoter and enhancer sequences and the like). The type of vector used herein is not specifically limited, although DNA vectors are preferred. Examples thereof can include viral vectors and plasmid vectors. The viral vector is not specifically limited, although retroviral vectors, adenoviral vectors, adeno-associated viral vectors, and the like can be employed. In addition, as to the above plasmids, mammalian expression plasmids well known to those skilled in the art can be employed.

As to confirming a nuclear reprogramming factor, for example, the screening method of nuclear reprogramming factor described in International Publication No. WO2005/80598 A1, incorporated by reference herein in its entirety, can be used. Those skilled in the art are able to screen a nuclear reprogramming factor for use in the method of the present invention by referring to the above publication. In addition, the nuclear reprogramming factor can also be confirmed by using a method in which appropriate modification or alteration has been made in the above screening method.

Methods for using a retrovirus as a vector, as well as exemplified combinations of DNAs encoding nuclear reprogramming factors (or nuclear reprogramming factor genes), are disclosed in WO 2007/69666 A1; Takahashi et al., *Cell* 126:663-676, 2006; and Takahashi et al., *Cell* 131:861-872, 2007, which are herein incorporated by reference in their entireties. Methods for using a lentivirus as a vector, as well as another combination of nuclear reprogramming factor genes, are disclosed in Yu et al., *Science* 318:1917-1920, 2007; and Shi et al., *Cell Stem Cell* 3: 568-574, 2008, which are herein incorporated by reference in their entirety. Shi et al. also disclose, for example, that small molecules such as BIX-01294 and BayK8644 can compensate for viral transduction of critical factors and improve reprogramming efficiency (see, e.g., Abstract). Methods for using adenovirus as a vector are disclosed in Stadtfeld et al., *Science* 322:945-949, 2008, which is herein incorporated by reference in its entirety. For example, Stadfeldt et al. disclose that iPS cells could be generated from fibroblasts and liver cells by using nonintegrating adenoviruses transiently expressing Oct4, Sox2, Klf4, and c-Myc (see, e.g., Abstract). Indeed, Stadtfeldt et al. disclose that 1 to 4 viral particles per cell were sufficient to infect 70 to 80% of cells with individual vectors, with an estimated 50-60% of cells expressing all four viral reprogramming factors (see, e.g., page 946, third column). Methods for using a plasmid as a non-viral vector are disclosed in U.S. Provisional Application No. 61/071,508; U.S. Provisional Application No. 61/136,246; U.S. Provisional Application No. 61/136,615; and U.S. Provisional Application No. 61/193,363 entitled "Method for Nuclear Reprogramming" filed Nov. 21, 2008; and Okita et al., *Science* 322:949-953, 2008, which are herein incorporated by reference in their entireties. U.S. Provisional Application No. 61/071,508 discloses many examples of non-viral expression vectors which may be used, including, for example, *Escherichia coli*-derived plasmids such as pBR322, pUC18, pUC19, pBluescript and the like, yeast-derived plasmids such as YEp13, YEp24, and the like, as well as other non-viral expression vectors such as pCMV6-XL3 (OriGene Technologies Inc.), EGFP-C1 (Clontech), pcDNAI (FUNAKOSHI), etc. (see, e.g., page 10, lines 2-20). Okita et al. disclose that repeated transfection of two expression plasmids, one containing cDNAs of Oct3/4, Sox2, and Klf4 and another containing the c-Myc cDNA, into mouse embryonic fibroblasts generated iPS cells (see, e.g., Abstract). For example, Okita et al. used a plasmid vector containing the CAG constitutively active promoter (and a foot-and-mouth disease virus 2A self-cleaving peptide sequence) to enable efficient (and polycistronic) expression of reprogramming factors (page 950 and FIG. 2). Similarly, U.S. Provisional Application No. 61/136,615 discloses that a single non-viral expression vector may be used which, for example, incorporates a plurality of nuclear reprogramming factors by using an intervening sequence such as the 2A sequence of foot-and-mouth disease virus, which enables polycistronic expression (see, e.g., paragraph bridging pages 19-20 and SEQ ID NO: 61). U.S. Provisional Application No. 61/136,615 also discloses that various establishment efficiency improvers may be introduced to increase the efficiency of iPS cell establishment, including, for example, histone deacetylase inhibitors, G9a histone methyltransferase inhibitors, nucleic acid-based expression inhibitors, and the like (see, e.g., paragraph bridging pages 25-26). One of ordinary skill in the art could choose and use an appropriate method from among the above known methods, or from any of the other known methods or vectors available in the prior art.

Nuclear reprogramming can be performed in the presence of miRNA in any number of ways. The manner of providing the miRNA is not specifically limited, although examples thereof can include a method for directly injecting miRNA into nuclei of somatic cells, and a method for introducing an appropriate recombinant vector capable of expressing miRNA into somatic cells. However, these methods are not to be considered as limiting.

The method for introducing a recombinant vector into somatic cells is not specifically limited, and can be carried out by any method well known to those skilled in the art. Examples of the employable methods can include transient transfection, microinjection, a calcium phosphate precipitation method, liposome-mediated transfection, DEAE dextran-mediated transfection, electroporation, and methods comprising the use of a gene gun.

Examples of the combination of genes encoding reprogramming factors are disclosed in International Publication No, WO2007/069666 A1 and its family member U.S. patent application Ser. No. 12/213,035 and U.S. patent application Ser. No. 12/289,873, filed Nov. 6, 2008, entitled "Nuclear Reprogramming Factor and Induced Pluripotent Stem Cells" which are incorporated by reference herein in their entireties. Those skilled in the art are able to appropriately select a gene that can be preferably used for the method of the present invention by referring to the above publication. In addition, other examples of the combinations of genes encoding reprogramming factors are disclosed, for example, in Yu et al., *Science* 318:1917-20, 2007, incorporated by reference herein in its entirety. Accordingly, those skilled in the art are able to understand the variety of the combination of genes encoding reprogramming factors, and are able to employ an appropriate combination of genes in the method of the present invention, which combination is not disclosed in International Publication No. WO2007/069666 A1 or Yu et al., *Science* 318:1917-20, 2007, by using the screening method of nuclear reprogramming factor described in International Publication No. WO2005/80598 A1.

Examples of the gene encoding a reprogramming factor that can be used for the method of the present invention can include: one or more gene(s) selected from an Oct family gene, a Klf family gene, a Sox family gene, a Myc family gene, a Lin family gene, and a Nanog gene; preferably one or more gene(s) selected from an Oct family gene, a Klf family gene, a Sox family gene, a Lin family gene, and a Nanog gene, and excluding a Myc family gene; one or more gene(s) selected from an Oct family gene, a Klf family gene, a Myc family gene, a Lin family gene, and a Nanog gene, and excluding a Sox family gene; more preferably a combination of two genes; yet more preferably a combination of three genes; and most preferably a combination of four genes. As a single nuclear reprogramming gene, an Oct3/4 family gene is preferred, and preferred as combinations of different genes are combinations of an Oct family gene with one or more other genes as mentioned above.

Regarding the Oct family gene, Klf family gene, Sox family gene, and Myc family gene, specific examples of these family genes are described in International Publication No. WO2007/069666 A1. Regarding the Lin family gene, those skilled in the art are able to extract the family gene in a similar way. Examples of the Lin family genes include, for example, Lin28 and Lin28b. The NCBI accession numbers of Lin28 are NM_145833 (mouse) and NM_024674 (human). The NCBI accession numbers of Lin28b are NM_001031772 (mouse) and NM_001004317 (human).

In addition, reprogramming factor(s) encoded by one or more gene(s) selected from an Oct family gene, a Klf family gene, a Sox family gene, a Myc family gene, a Lin family gene, and a Nanog gene, may be substituted by, for example a cytokine, or one or more other low molecular weight compound(s) in some cases. Examples of such low molecular weight compound(s) can include low molecular weight compounds having an enhancing action on the expression of one or more gene(s) selected from an Oct family gene, a Klf family gene, a Sox family gene, a Myc family gene, a Lin family gene, and a Nanog gene. Those skilled in the art are able to readily screen such low molecular weight compound(s).

More preferable gene or combinations of genes are as follows:
(a) a combination of two genes comprising an Oct family gene and a Sox family gene;
(b) a combination of three genes comprising an Oct family gene, a Klf family gene, and a Sox family gene;
(c) a combination of four genes comprising an Oct family gene, a Sox family gene, a Lin family gene, and a Nanog gene;
(d) a combination of four genes comprising an Oct family gene, a Klf family gene, a Sox family gene, and a Myc family gene;
(e) an Oct family gene alone;
(f) a combination of two genes comprising an Oct family gene and a Klf family gene;
(g) a combination of two genes comprising an Oct family gene and a Nanog gene; and
(h) a combination of three genes comprising an Oct family gene, a Klf family gene, and a Myc family gene.
However, the above-mentioned combinations are not to be considered as limiting.

All of these genes are commonly present in mammals, including human. In order to use the above genes according to the present invention, genes derived from any mammal (for example, primates (e.g., human, monkey, chimpanzee, etc.), rodents (e.g., mouse, rat, hamster, etc.), ungulates (e.g., cattle, sheep, horse, pig, etc.), pet animals (e.g., dog, cat, etc.), and so on) can be employed. The genes may be cDNAs for them. In addition, it is also possible to use a wild type gene product, as well as mutant gene products in which several amino acids (for example 1 to 10 amino acids, preferably 1 to 6 amino acids, more preferably 1 to 4 amino acids, yet more preferably 1 to 3 amino acids, and most preferably 1 or 2 amino acids) have been substituted, inserted, and/or deleted, and which have comparable equivalent functions to those of the wild type gene product. For example, as to the c-Myc gene product, a stable type variant, e.g., (T58A) and the like may also be used as well as the wild type. The same principle can be applied to other gene products.

In addition to the above genes, a gene encoding a factor which induces immortalization of cells may also be combined. As disclosed in International Publication No. WO2007/069666 A1, for example, one or more gene(s) selected from a TERT gene, and following genes: SV40 Large T antigen, HPV16 E6, HPV16 E7, and Bmi1, can be either solely used or jointly used in an appropriate combination.

Further preferable combinations are as follows, for example:
(a) a combination of four genes comprising an Oct family gene, a Klf family gene, a Sox family gene, and a TERT gene;
(b) a combination of four genes comprising an Oct family gene, a Klf family gene, a Sox family gene, and a SV40 Large T antigen gene; and
(c) a combination of five genes comprising an Oct family gene, a Klf family gene, a Sox family gene, a TERT gene, and a SV40 Large T antigen gene.
The Klf family gene may be omitted from the above combinations.

Examples of respective members of the Oct family, Klf family, Sox family, Myc family, Lin family, and Nanog family include, but are not limited to: Oct3/4 (also referred to as Oct3, Oct4 or POU5F1) for Oct family; Sox1, Sox2, Sox3, Sox4, Sox11 and Sox15 for Sox family; c-Myc, N-Myc and L-Myc for Myc family; Lin28 and Lin28b for Lin family; and Nanog for Nanog family.

Further, in addition to the above genes, one or more gene(s) selected from ECAT3 (also referred to as Fbx15), ECAT5 (also referred to as ERas), ECAT15-2, Tcl1, and β-catenin (also referred to as Ctnnbl) may be combined, and/or one or more gene(s) selected from ECAT1, ECAT2 (also referred to as ESG1), ECAT7, ECAT8, ECAT9 (also referred to as Gdf3), ECAT10 (also referred to as Sox15), ECAT15-1 (also referred to as Dppa4), Esg1, Dnmt3L, ECAT8, Gdf3, Fthl17, Sall4, Rex1, Utf1, Stella, Stat3, Grb2, Myb12, FoxD3, ZNF206, and Otx2 may also be combined. These combinations are specifically described in International Publication No. WO2007/069666 A1.

The amino acid and nucleotide sequences of nuclear reprogramming factors usable alone or in combination in the present application, for example Oct3/4 Nanog, Lin28, Lin28b, ECAT1, ECAT2, ECAT3, ECAT5, ECAT7, ECAT8, ECAT9, ECAT10, ECAT15-1, ECAT15-2, Fthl17, Sall4, Rex1, Utf1, Tcl1, Stella, β-catenin, Stat3, Grb2, c-Myc, N-Myc, L-Myc, Sox1, Sox2, Sox3, Sox4, Sox11, Myb12, Klf1, Klf2, Klf4, and Klf5; and FoxD3, ZNF206, and Otx2 (which are also described in International Publication No.

WO2008/118820), are available from GenBank (NCBI, USA). Accession numbers thereof regarding human, mouse or rat are described below:

Oct3/4 (human NM_203289 or NM_002701, mouse NM_013633, rat NM_001009178), Nanog (human NM_024865, mouse NM_028016, rat NM_001100781), Lin28 (human NM_024674, mouse NM_145833, rat NM_001109269), Lin28b (human NM_001004317, mouse NM_001031772), ECAT1 (human AB211062, mouse AB211060), ECAT2 (human NM_001025290, mouse NM_025274), ECAT3 (human NM_152676, mouse NM_015798), ECAT5 (human NM_181532, mouse NM_181548), ECAT7 (human NM_013369, mouse NM_019448), ECAT8 (human AB211063, mouse AB211061), ECAT9 (human NM_020634, mouse NM_008108), ECAT10 (human NM_006942NM_009235, mouse NM_009235), ECAT15-1 (human NM 018189, mouse NM_028610), ECAT15-2 (human NM_138815NM_028615, mouse NM_028615), Fthl17 (human NM_031894, mouse NM_031261), Sall4 (human NM_020436, mouse NM_175303), Rex1 (human NM_174900, mouse NM_609556), Utf1 (human NM_003577, mouse NM_009482), Tcl1 (human NM_021966, mouse NM_009337), Stella (human NM_199286, mouse NM_139218), β-catenin (human NM_001904, mouse NM_007614), Stat3 (human NM_139276, mouse NM_213659), Grb2 (human NM_002086, mouse NM_008163), FoxD3 (human NM_012183, mouse NM_010425), ZNF206 (human NM_032805, mouse NM_001033425), Myb12 (human NM_002466, mouse NM_008652), Otx2 (human NM_172337, mouse NM_144841), c-Myc (human NM_002467, mouse NM_010849), N-Myc (human NM_005378, mouse NM_008709), L-Myc (human NM_005376, mouse NM_008506), Sox1 (human NM_005986 NM_005986, NM_009233, mouse NM_005986, NM_009233), Sox2 (human NM_003106, mouse NM_011443), Sox3 (human NM_005634, mouse NM_009237), Sox4 (human NM_003107, mouse NM_009238), Sox11 (human NM_003108, mouse NM-009234), Myb12 (human NM-002466, mouse NM_008652), Klf1 (human NM-006563, mouse NM_010635), Klf2 (human NM_016270, mouse NM_008452), Klf4 (human NM_004235, mouse NM_010637), and Klf5 (human NM_001730, mouse NM-009769).

Particularly preferable combinations of genes are as follows:
(1) a combination of two genes comprising Oct3/4 and Sox2 genes;
(2) a combination of three genes comprising Oct3/4, Klf4, and Sox2 genes;
(3) a combination of four genes comprising Oct3/4, Sox2, Lin28, and Nanog genes;
(4) a combination of four genes comprising Oct3/4, Sox2, TERT, and SV40 Large T antigen genes;
(5) a combination of five genes comprising Oct3/4, Klf4, Sox2, TERT, and SV40 Large T antigen genes;
(6) a combination of two genes comprising Oct3/4 and Klf4 genes;
(7) a combination of three genes comprising Oct3/4, Klf4, and c-Myc genes;
(8) a combination of four genes comprising Oct3/4, Sox2, Klf4, and c-Myc genes;
(9) an Oct3/4 gene alone; and
(10) a combination of two genes comprising Oct3/4 and Nanog genes.

However, these combinations are not to be considered as limiting.

The factors including the gene products as mentioned above may further be combined with one or more gene product(s) of gene(s) selected from: Fbx15, Nanog, ERas, ECAT15-2, Tcl1, and β-catenin. Further, these factors may also be combined with one or more gene product(s) of gene(s) selected from: ECAT1, Esg1, Dnmt3L, ECAT8, Gdf3, Sox15, ECAT15-1, Fthl17, Sall4, Rex1, UTF1, Stella, Stat3, and Grb2, for example. However, gene products that can be included in the nuclear reprogramming factors of the present invention are not limited to the gene products of genes specifically described above. The nuclear reprogramming factors of the present invention can include other gene products which can function as a nuclear reprogramming factor, as well as one or more factors involving differentiation, development, or proliferation, and factors having other physiological activities. It should be understood that the aforementioned aspect may also be included within the scope of the present invention.

As mentioned above, in the present invention, the nuclear reprogramming factors can be employed in the form of proteins (or gene products or polypeptides) or in the form of nucleic acids (or genes, DNAs, RNAs, or polynucleotides). Such proteins or nucleic acids can be routinely prepained by means of conventional techniques such as polymerase chain reaction (PCR) techniques, gene engineering techniques, and hybridization techniques. Also, on the basis of known sequences of genes from certain classes of animals, analogous nucleic acids from other animals can be isolated from tissue or genomic libraries. Genera techniques as mentioned above are described in Sambrook, J. et al., Molecular Cloning: A Laboratory Manual, 2nd edition, Cold Spring Harbor Laboratory Press (1989), Ausubel, F. M. et al., Short protocols in Molecular Biology: A Compendium Methods from Current Protocols in Molecular Biology, John Wiley & Sons (1999), etc., for example.

Moreover, to enhance an efficiency to establish induced pluripotent stem (iPS) cells, the following cytokines and/or small molecules, besides the above-mentioned miRNAs, may further be introduced into somatic cells to be reprogrammed: i.e., basic fibroblast growth factor (bFGF), stem cell factor (SCF), etc. for the cytokines; and histone deacetylase inhibitors such as valpronic acid, DNA methylase inhibitors such as 5'-azacytidine, histone methyltransferase (G9a) inhibitors such as BIX01294 (BIX), etc. for the small molecules (D. Huangfu et al., *Nat. Biotechnol.*, 26, pp. 795-797, 2008; S. Kubicek et al., *Mol. Cell*, 25, pp. 473-481, 2007; Y. Shi et al., *Cell Stem Cell*, 3, 568-574, 2008, Yan Shi et al., *Cell Stem Cell*, 2, pp. 525-528, 2008. In addition, p53 inhibitors such as shRNA or siRNA for p53 and/or UTF1 may be intoroduced into somatic cells (Yang Zhao et al., *Cell Stem Cell*, 3, pp 475-479, 2008). Also, activation of the Wnt signal (Marson A. et al., *Cell Stem Cell*, 3, pp 132-135, 2008) or inhibition of signaling by mitogen-activated protein kinase or glycogen synthase kinase-3 (Silva J. et al., *PloS Biology*, 6, pp 2237-2247 2008) can serve as a means for increasing the efficiency of generating iPS cells.

Among these genes, if one or more gene product(s) is/are already expressed in somatic cells to be reprogrammed, such gene products can be excluded from the factors to be introduced. For example, one or more gene(s) besides the already-expressed gene(s) can be introduced into somatic cells by an appropriate gene introduction method, for example, a method using a recombinant vector. Usable vectors include, but are not limited to, viral vectors, plasmids, and the like. Examples of the viral vectors include retro viral vectors, rentiviral vectors, adenoviral vectors, adeno-associated vectors, etc. Examples of the plasmids include plasmids for mammalian cells.

Where two or more nuclear reprogramming factor genes (or DNAs) are introduced into somatic cells, a cesste can be constructed by ligating plural genes in tandem, and then inserted into a vector. To each gene can be ligated control sequences such as promoter, enhancer, ribosome binding sequence, terminator, and polyadenylation site, so that said respective genes can be expressed. Alternatively, the respective genes may be separately inserted into different vectors so that they can be expressed. The vectors may further comprise a selectable marker sequence such as a drug resistance gene (e.g., kanamycin resistance gene, ampicillin resistance gene, or puromycin resistance gene, or thymidin kinase gene, diphtheria toxin gene) or a reporter gene sequence such as green fluorescent protein (GFP), β-gluclonidase (GUS), or FLAG.

Furthermore, the nuclear reprogramming factors may be proteins per se prepared from DNAs encoding them, or fusion proteins thereof with another polypeptide or peptide, such as histidin tags to facilitate the purification of the nuclear reprogramming factor proteins and an HIV virus-derived TAT peptide to facilitate the internalization of the nuclear reprogramming factors through the membrane of a somatic cell.

Among the above-mentioned genes, if one or more gene product(s) is/are introduced into nuclei by a technique such as addition of an HIV virus-derived TAT peptide and/or nuclear localization signal to form a fusion protein or by a technique such as nuclear microinjection, or simply by addition of a small molecule capable of diffusing across the plasma membrane, the other one or more gene(s) can be introduced by an appropriate gene introduction method, for example, a method using a recombinant vector.

In addition, a gene product serving as a nuclear reprogramming factor may be either a protein itself produced from the abovementioned gene, or in the form of a fusion gene product between such a protein and another protein, a peptide, or the like. For example, a fusion protein having Green Fluorescent Protein (GFP) and a fusion gene product having a peptide such as a histidine tag may also be used. Further, use of a prepared fusion protein having a HIV virus-derived TAT peptide enables the promotion of endocytosis of a nuclear reprogramming factor through cell membrane, and also enables the induction of reprogramming by simply adding such a fusion protein into the medium while avoiding complicated manipulations such as gene introduction. The preparation method of the aforementioned fusion gene product is well known to those skilled in the art, and therefore those skilled in the art are able to readily design and prepare an appropriate fusion gene product according to the purpose.

In this application, the term "induced pluripotent stem cells (iPS cells)" refers to cells having similar properties to those of ES cells, and more specifically the term includes undifferentiated cells which are reprogrammed from somatic cells and have pluripotency and proliferation potency. However, this term is not to be construed as limiting in any sense, and should be construed to have its broadest meaning. The preparation method of induced pluripotent stem cells with the use of a nuclear reprogramming factor is described in International Publication No. WO2005/80598 A1 (the term "ES-like cell" is used in this publication), and methods for isolating induced pluripotent stem cells are also specifically described. In addition, specific examples of the reprogramming factor and specific examples of the reprogramming method of somatic cells with use of such a reprogramming factor are disclosed in International Publication No. WO2007/069666 A1. Accordingly, it is desirable for those skilled in the art to refer to these publications for carrying out the present invention.

The preparation method of induced pluripotent stem cells from somatic cells by the method of the present invention is not specifically limited, and any method can be employed as long as the method enables nuclear reprogramming of somatic cells with a nuclear reprogramming factor in the presence of miRNA in an environment where somatic cells and induced pluripotent stem cells can grow. For example, a vector comprising a gene which can express a nuclear reprogramming factor can be used to introduce such a gene into somatic cells, and at either the same or different timing, a recombinant vector which can express miRNA or precursor RNAs thereof (e.g., pri-miRNAs or pre-miRNAs) can be introduced into the somatic cells. In the cells the miRNAs can be produced from the precursor RNAs. If such vectors are used, two or more genes may be incorporated into a vector to effect simultaneous expression of respective gene products in somatic cells.

When nuclear reprogramming factor gene(s) and/or miRNA(s) are introduced into somatic cells with use of at least one vector which can express the above gene(s) or miRNA(s), the expression vector may be introduced into somatic cells that have been cultured on feeder cells, or the expression vector may also be introduced into somatic cells without feeder cells. The latter method is sometimes more suitable in order to improve the introduction efficiency of the expression vector. The miRNAs may be introduced directly without vector into somatic cells. For introduction of a vector or mIRNA, known techniques, such as microinjection, liposome, lipofection, electroporation, calsium phosphate, and viral infection, may be used. The viral infection using retrovirus or rentivirus vector is described in prior art (e.g., *Cell*, 126:663-676, 2006; *Cell*, 131:861-872, 2007; or *Science*, 318:1917-1920, 2007). The use of adenovius vector is described in *Science*, 322:945-949 (2008), wherein specific means for use of a plasmid is taught too (*Science*, 322:949-953 (2008)).

As to the feeder cells, there may be appropriately used feeder cells for use in culture of embryonic stem cells. Examples thereof can include primary culture cells of 14 or 15 day-mouse embryonic fibroblasts and STO cells of fibroblast cell line, which are treated with either radiation or a drug such as mitomycin C.

The culture of somatic cells introduced with a nuclear reprogramming factor under an appropriate condition leads to autonomous nuclear reprogramming, as a result of which induced pluripotent stem cells can be produced from somatic cells. The process for introducing a gene encoding a nuclear reprogramming factor and/or miRNA into somatic cells with use of an expression vector to thereby obtain induced pluripotent stem cells can be performed in accordance with, for example, a method using a retrovirus. Examples of such method include methods described in publications such as Takahashi et al., *Cell* 126:663-76, 2006; Takahashi et al., *Cell* 131:861-72, 2007; Yu et al., *Science* 318:1917-20, 2007. When human induced pluripotent stem cells are to be produced, it is desirable to set the cell culture density after the introduction of an expression vector to be lower than normal cases for culturing animal cells. For example, it is preferable to keep culturing at a density of $1 \times 10^4$ to $1 \times 10^5$ cells/10 cm dish, and more preferably about $5 \times 10^4$ cells/10 cm dish. The medium for use in culture is not specifically limited, and can be appropriately selected by those skilled in the art, although for example it is sometimes preferable to use a medium suitable for human ES cell culture for the production of human induced pluripotent stem cells. The medium selection and culture condition can be referred to the above publications.

Examples of the culture media to induce iPS cells include, but are not limited to, (1) DMEM, DMEM/F12, or DME medium supplemented with 10-15% FBS, which medium may optionally contain leukemia inhibiting factor (LIF), penicillin/streptomycin, puromycin, L-glutamin, non-essential amino acids, β-mercaptoethanol, or the like), and (2) a medium ofr culture of ES cells supplemented with bFGF or SCF, such as murine ES cell culture medium (e.g., TX-WES medium, Thromb-X) or primate ES cell culture medium (e.g., primate (human or monkey) ES cell culture, Repro-CELL (Kyoto, Japan)).

The procedure of the culture may comprise contacting somatic cells with at least one nuclear reprogramming factor or DNA encoding it (preferably, a vector) on a DMEM or DMEM/F12 medium containing 10% FBS in the presence of 5% $CO_2$ at 37° C., followed by culturing them for about 4-7 days, subsequently reseeding the cells on feeder cells (e.g., STO or SNL cells pretreated with mitomycin C), and from about day 10 after contact, culturing the cells on primate ES cell culture medium supplemented with bFGF, thereby obtaining iPS cell-like colonies after about 30-45 days of the contact. This procedure is suitable for induction of primate iPS cells including human iPS cells.

Alternatively, another procedure may comprise contacting somatic cells with at least one nuclear reprogramming factor or DNA encoding it (preferably, a vector) on feeder cells (e.g., STO or SNL cells pretreated with mitomycin C) in the presence of 10% FFBS containing DMEM medium (which further contains LIF, penicillin/streptomycin, puromycin, L-glutamin, non-essential amino acids, and β-mercaptoethanol) under 5% $CO_2$ at 37° C., followed by culturing them for about 25-30 days to induce iPS cell-like colonies. This procedure is suitable for induction of rodent iPS cells.

During the above-mentioned cultures, the medium is exchanged with a fresh medium once a day from day 2 after start of a culture. The number of somatic cells used for reprogramming may be ranged from approximately $5 \times 10^3$ cells to approximately $5 \times 10^6$ cells per 100 $cm^2$ of culture dish.

The iPS cell-like colonies on the dish are treated with a CTK solution (which contains trypsin and cllagenase IV), and subsequently the residual colonies are seeded on the above-mentioned feeder cells followed by culturing them on the ES cell culture medium. By the procedure, passages of iPS cells can be conducted.

Thus produced induced pluripotent stem cells can be checked with various markers specific to undifferentiated cells, and the means therefor is described in the above publications specifically in detail, for example, it is a method of RT-PCR. For example, some pluripotent cell markers include: Oct3/4; Nanog; alkaline phosphatase (AP); ABCG2; stage specific embryonic antigen-1 (SSEA-1); SSEA-3; SSEA-4; Tra-1-60; TRA-1-81; Tra-2-49/6E; ERas/ECAT5, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); and T-cell lymphoma breakpoint 1 (Tcl1); DPPA3/Stella; DPPA4. Other markers can include Dnmt3L; Sox15; Stat3; Grb2; SV40 Large T Antigen; HPV16 E6; HPV16 E7, β-catenin, and Bmi1. Such cells can also be characterized by the down-regulation of markers characteristic of the differentiated cell from which the iPS cell is induced. For example, iPS cells derived from fibroblasts may be characterized by down-regulation of the fibroblast cell marker Thy1 and/or up-regulation of SSEA-3 and 4. It is understood that the present invention is not limited to those markers listed herein, and encompasses markers such as cell surface markers, antigens, and other gene products including ESTs, RNA (including microRNAs and antisense RNA), DNA (including genes and cDNAs), and portions thereof.

Beside detection of expression of ES cell specific markers, iPS cells may be further identified by semipermanent cell proliferation, pluripotency, or cell morphology (Takahashi, K. et al., *Cell* 131:861-872 (2007)).

Briefly, as to the semipermanent proliferation, whether cells expand exponentially is tested by culturing the cells over about 4-6 months. In case of human iPS cells, because the population doubling time is known to be about 46.9±12.4 hr, 47.8±6.6 hr, or 43.2±11.5 hr for example, this value can be indicative of the ability of proliferation. Alternatively, high telomerase activity may be detected by the telomeric repeat amplification protocol (TRAP) because iPS cells normally have high telomerase activity.

As to the pluripotency, this ability can be confirmed by forming teratoma and identifying tissues or cells of three embryonic germ layers (i.e., ectoderm, mesoderm, and endoderm). Specifically, cells are injected intradermaly in a nudemouse (where the cells are induced from murine somatic cells) or in the spermary of a SCID mouse (where the cells are induced from human somatic cells), followed by confirming the formation of tumore then confirming that the tumor tissues are composed of tissues including neural rosettes (ectoderm), cartilage (mesoderm), cardiac myocyte (mesoderm), gut-like epithelium (endoderm), adipose (mesoderm), and the like.

As to the morphology of cells, because human or mouse iPS cell colony is known to have a morphology similar to that of human or mouse ES cell colony, the morphology of iPS cell colony can be used as an indicator. In general, human iPS cells form flat colonies, while mouse iPS cells tend to form swollen colonies.

Various media capable of retaining undifferentiation property and pluripotency of ES cells and various media incapable of retaining these properties are known in the art, and appropriate combination of these media enables efficient isolation of induced pluripotent stem cells. The differentiation ability and proliferation potency of thus isolated induced pluripotent stem cells can be readily checked by those skilled in the art, with use of general checking means for ES cells. In addition, colonies of induced pluripotent stem cells can be obtained by growing thus produced induced pluripotent stem cells under an appropriate condition, and the presence of these induced pluripotent stem cells can be identified with reference to the shape of their colonies. For example, it is known that mouse induced pluripotent stem cells form swollen colonies, while human induced pluripotent stem cells form flat colonies. These colony shapes are respectively very similar to those of mouse ES cells and human ES cells, and those skilled in the art are thus able to identify these produced induced pluripotent stem cells with reference to the shape of their colonies.

The types of somatic cells to be reprogrammed by the method of the present invention are not specifically limited, and any somatic cells can be used. For example, somatic cells from any mammal (for example, human, chimpanzee, mouse, monkey, rat, hamster, guinea pig, cattle, sheep, goat, pig, horse, dog, or cat) can be employed. Preferable mammals are human and mouse. Not only embryonic somatic cells but also neonatal somatic cells, matured somatic cells, tissue stem cells, tissue precursor cells, cultured primary cells, subcultured cells, and cell lines, may also be used. For example, various somatic cells such as (1) tissue stem cells, e.g., neural stem cells, hematopoietic stem cells, mesenchymal stem cells, and dentis stem cells; (2) tissue precursor cells; and (3) differentiated cells, e.g., lymphocytes, epidermal cells, endotherial cells, muscle cells, fibroblast cells, pilary cells, skin cells, liver cells, gastric mucosa cells, intestine cells, spleen cells, pancreatic cells (including pancreatic exocrine cells), brain cells, lung cells, and renal cells can be reprogrammed. For use of induced pluripotent stem cells in therapies against diseases, it is desirable to use somatic cells isolated from the patient. For example, somatic cells involved in a disease and somatic cells associated with a therapy for a disease can also be used.

The application of induced pluripotent stem cells produced by the method of the present invention is not specifically limited, and these cells can be used for every examination/study to be performed with use of ES cells, and for any disease therapy which utilizes ES cells. For example, induced pluripotent stem cells obtained by the method of the present invention can be induced into desired differentiated cells or precursor cells (such as nerve cells, myocardial cells, blood cells and insulin-producing cells) or by treatment with retinoic acid, a growth factor such as EGF, glucocorticoid, activin A/BMP4 (bone morphogenetic protein 4), or VEGF (vascular endothelial growth factor), so that appropriate tissues can be formed. Stem cell therapies through autologous cell transplantation can be achieved by returning these differentiated cells or tissue obtained in the above manner, into the patient. However, the application of the induced pluripotent stem cells (iPS cells) of the present invention is not to be limited to the abovementioned specific aspects. The iPS cells have a capacity of germline transmission in vivo. Thus, when the iPS cells are introduced into the blastocyst from a non-human mammal, and then transplant the cells into the uterus of a surrogate mother of the same animal, thereby creating chimeric animals to which part of the genotypes of the iPS cell has been transmitted (WO 2007/069666). The iPS cells can also be used for modification of a gene, introduction (or knock-in) of a gene, or knock-out of a gene, thereby enabling to clarify the function of a gene, to create a non-human animal model with disease, or to produce a substance such as protein.

EXAMPLES

The present invention will be explained more specifically with reference to the following examples. However, the scope of the present invention is not limited to these examples.

Example 1: Preparation of Induced Pluripotent Stem Cells Through Nuclear Reprogramming of Mouse Embryonic Fibroblasts pMXs-based retroviral vectors, which respectively encode each of three genes of mouse-derived Oct3/4, Sox2, and Klf4, control DsRed or each miRNA of 18 types of miRNAs, were transfected into PLAT-E cells using FuGENE 6 reagent (Roche) to get retroviruses. On the next day, embryonic fibroblasts (Nanog GFP MEF, WO2007/069666 A1) derived from transgenic mice generated by insertion of sequences encoding EGFP gene and puromycin resistance gene downstream of a Nanog gene promoter region, were seeded at $1 \times 10^5$ cells/well in 6-well plates. On the next day, these cells were infected with retroviruses expressing Oct3/4, Sox2, Klf4, and each type of miRNA selected from 18 types of miRNAs, at a ratio of 1 ml of virus mixture expressing these three factors to 1 ml of virus solution expressing miRNA or DsRed, so as to prepare induced pluripotent stem cells through nuclear reprogramming.

TABLE 1

| miRNA number | miRNA sequence (other name(s) indicated in parentheses) | miRBase accession number |
| --- | --- | --- |
| 1 | mmu-miR-150 | MI0000172 |
| 2 | mmu-miR-182 | MI0000224 |
| 3 | mmu-miR-126 | MI0000153 |
| 4 | mmu-miR-290-295 cluster | |
| 5 | mmu-miR-290 (mmu-miR-290-5p/290-3p) | MI0000388 |
| 6 | mmu-miR-291a (mmu-miR-291a-5p/291a-3p) | MI0000389 |
| 7 | mmu-miR-292 (mmu-miR-292-5p/292-3p) | MI0000390 |
| 8 | mmu-miR-294 (mmu-miR-294/294*) | MI0000392 |
| X(9) | mmu-miR-295 (mmu-miR-295/295*) | MI0000393 |
| 10 | mmu-miR-17-92 cluster | |
| 11 | mmu-miR-323 | MI0000592 |
| 12 | mmu-miR-130b | MI0000408 |
| 13 | mmu-miR-7a-1 | MI0000728 |
| 14 | mmu-miR-7a-2 | MI0000729 |
| 15 | mmu-miR-205 | MI0000248 |
| 16 | mmu-miR-200a | MI0000554 |
| 17 | mmu-miR-200c | MI0000694 |
| 18 | mmu-miR-mix | |

*indicates star form of miRNA.

From the third day after infection, the cells were cultured in an ES cell medium containing LIF. On the fourth day after infection, the cells were harvested by trypsinization, and the whole amount thereof was spread over mytomicin-C treated STO cells as feeder cells. Every other day thereafter, the ES cell medium containing LIF was replaced. From the 21st day after infection, drug selection was started with addition of puromycin at a final concentration of 1.5 µg/ml. On the 28th day, the number of Nanog GFP positive colonies (GFP, the expression of which is induced by a Nanog gene promoter region, can be observed with the use of fluorescent microscopy) was counted. As a control, DsRed was used in place of miRNA. The results are shown in FIG. 1. It was found that mmu-miR-294 and mmu-miR-295 could respectively improve the nuclear reprogramming efficiency when introduced into mouse embryonic fibroblasts together with three factors of Oct3/4, Sox2, and Klf4, and could enable efficient establishment of induced pluripotent stem cells.

Example 2: Preparation of Induced Pluripotent Stem Cells Through Nuclear Reprogramming of Mouse Tail Tip Fibroblasts pMXs-based retroviral vectors, which respectively encode each of three genes of mouse-derived Oct3/4, Sox2, and Klf4, DsRed (control), or mmu-miR-295, were transfected into PLAT-E cells using FuGENE 6 reagent (Roche) to get retroviruses. On the next day, tail tip fibroblasts (Nanog GFP tailtip fibroblasts) derived from transgenic mice generated by insertion of sequences encoding EGFP gene and puromycin resistance gene downstream of a Nanog gene promoter region, were seeded at $1\times10^5$ cells/well in 6-well plates. On the next day, these cells were infected with retroviruses expressing three factors of Oct3/4, Sox2, and Klf4, and either DsRed or mmu-miR-295, at a ratio of 1:1:1:1, so as to prepare induced pluripotent stem cells through nuclear reprogramming.

Figure 2:
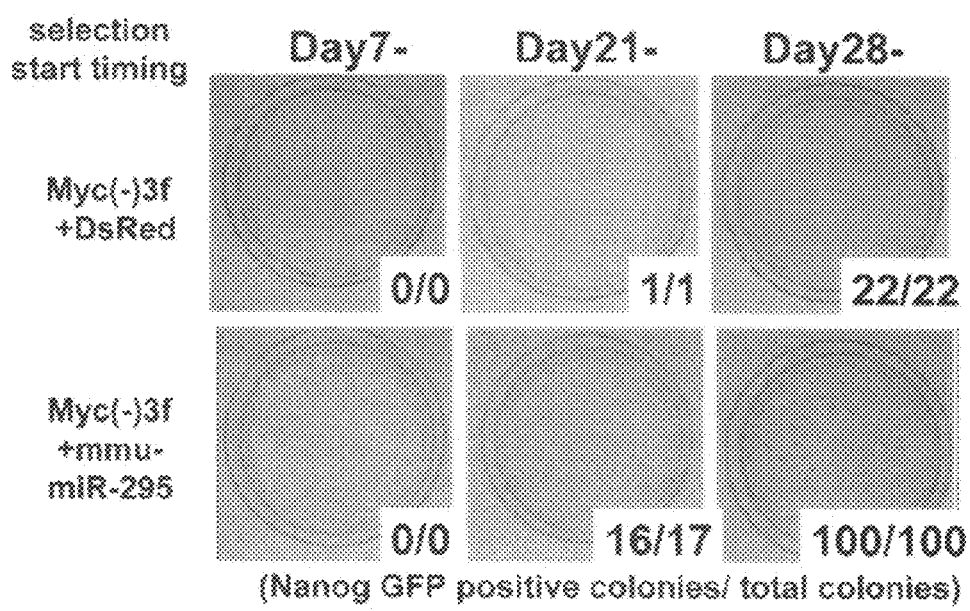
FIG. 2 shows the production efficiency of induced pluripotent stem cells. The top row of images shows the results of nuclear reprogramming in mouse tail tip fibroblasts (TTFs) when DsRed was added, as a control, to the combination of three genes comprising Oct3/4, Klf4, and Sox2 (a combination of three genes in which c-Myc was omitted from the combination of four genes). The bottom row of images shows the results of induction of nuclear reprogramming in mouse TTFs with the combination of three genes comprising Oct3/4, Klf4, and Sox2 in the presence of mmu-miR-295. The number in the figure indicates the number of Nanog GFP positive colonies/the number of total colonies on days 7, 21, and 28 after drug selection was started.

Since the third day after infection, the cells were cultured in an ES cell medium containing LIF. On the fourth day after infection, the cells were harvested by trypsinization and the whole amount thereof was spread over mytomicin-C treated STO cells as feeder cells. Every other day thereafter, the ES cell medium containing LIF was replaced. From the 7th, 21st, or 28th day after infection, drug selection was started with addition of puromycin at a final concentration of 1.5 µg/ml. On the 39th day, the number of total colonies and the number of Nanog GFP positive colonies (GFP, the expression of which is induced by Nanog promoter region, can be observed with fluorescent microscopy) were counted. The results are shown in FIG. 2. It was found that mmu-miR-295 could improve the nuclear reprogramming efficiency when introduced into mouse tail tip fibroblasts together with three factors of Oct3/4, Sox2, and Klf4, and could accelerate the reprogramming speed and enable efficient establishment of induced pluripotent stem cells.

Example 3: Preparation of Induced Pluripotent Stem Cells Through Nuclear Reprogramming of Adult Human Dermal Fibroblasts pMXs-based retroviral vectors, which encode three genes of human-derived OCT3/4, SOX2, and KLF4, and control DsRed or either 23 types of miRNAs or an miRNA cluster, were transfected into PLAT-E cells using FuGENE 6 reagent (Roche) to get retroviruses. On the next day, adult human dermal fibroblasts (aHDF) which were generated to express a rodent ecotropic virus receptor Slc7a1 (aHDF-Slc7a1), were seeded at $3\times10^5$ cells/well in 6-cm dishes. On the next day, the cells were infected with retroviruses expressing three genes of OCT3/4, SOX2, KLF4, and various types of miRNAs, at a ratio of 1:1:1:1, so as to produce induced pluripotent stem cells through nuclear reprogramming.

TABLE 2

| miRNA number | miRNA sequence (other name(s) indicated in parentheses) | miRBase accession number |
|---|---|---|
| 1 | hsa-miR-371 (hsa-miR-371-5p/371-3p) | MI0000779 |
| 2 | hsa-miR-372 | MI0000780 |
| 3 | hsa-miR-373 (hsa-miR-373/373*) | MI0000781 |
| 4 | hsa-miR-371-373 cluster | |
| 5 | hsa-miR-93 (hsa-miR-93/93*) | MI0000095 |
| 6 | hsa-miR-302a (hsa-miR-302a/302a*) | MI0000738 |
| 7 | hsa-miR-302b (hsa-miR-302b/302b*) | MI0000772 |
| 8 | hsa-miR-302c (hsa-miR-302c/302c*) | MI0000773 |
| 9 | hsa-miR-302d (hsa-miR-302d/302d*) | MI0000774 |
| 10 | hsa-miR-367 (hsa-miR-367/367*) | MI0000775 |
| 11 | hsa-miR-302-367 cluster | |
| 12 | hsa-miR-520a (hsa-miR-520a-5p/520a-3p) | MI0003149 |
| 13 | hsa-miR-520b | MI0003155 |
| 14 | hsa-miR-520c (hsa-miR-520c-5p/520c-3p) | MI0003158 |
| 15 | hsa-miR-520d (hsa-miR-520d-5p/520d-3p) | MI0003164 |
| 16 | hsa-miR-520e | MI0003143 |
| 17 | mmu-miR-290-295 cluster | |
| 18 | mmu-miR-290 (mmu-miR-290-5p/290-3p) | MI0000388 |
| 19 | mmu-miR-291a (mmu-miR-291a-5p/291a-3p) | MI0000389 |
| 20 | mmu-miR-292 (mmu-miR-292-5p/292-3p) | MI0000390 |
| 21 | mmu-miR-293 (mmu-miR-293/293*) | MI0000391 |
| 22 | mmu-miR-294 (mmu-miR-294/294*) | MI0000392 |
| 23 | mmu-miR-295 (mmu-miR-295/295*) | MI0000393 |

Figure 3:
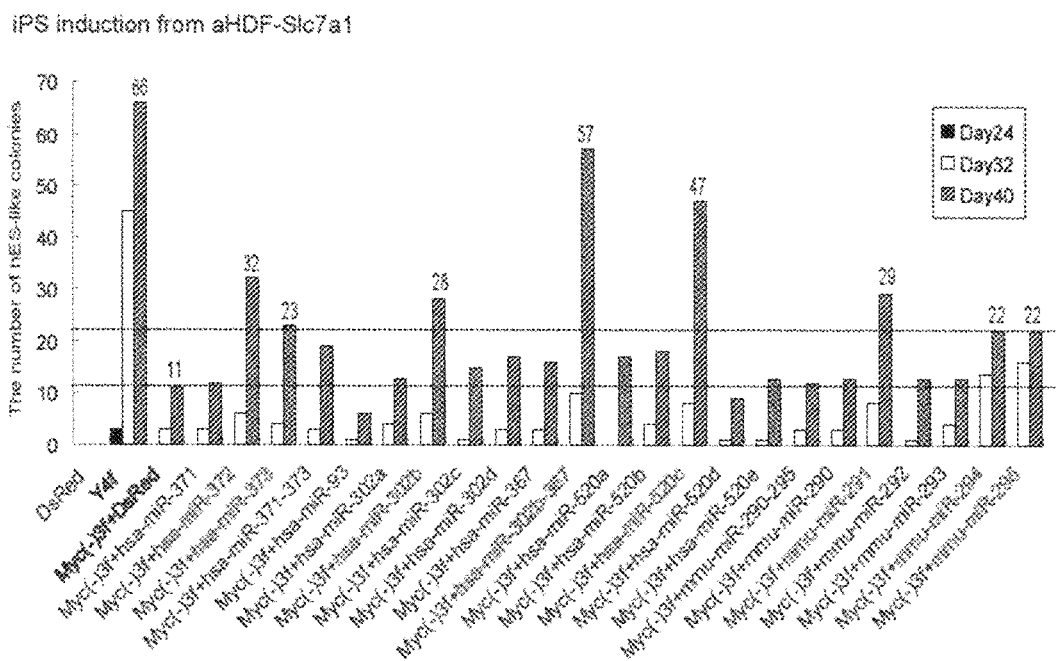
FIG. 3 shows the results of confirmation on the production efficiency of induced pluripotent stem cells through induction of nuclear reprogramming in adult human dermal fibroblasts expressing the mouse ecotropic virus receptor Slc7a1 gene using lentivirus (aHDF-Slc-7a1) with the combination of three genes comprising Oct3/4, Klf4, and Sox2 (Myc(−)3f: a combination of three genes in which c-Myc was omitted from the combination of four genes comprising Oct3/4, Klf4, Sox2, and c-Myc), or the combination of four genes comprising Oct3/4, Klf4, Sox2, and c-Myc (Y4f), in the presence of various miRNAs.

On the sixth day after infection, the cells were harvested by trypsinization and the whole amount of $5\times10^5$ cells was spread over on mytomicin-C treated STO cells as feeder cells. Every other day thereafter, human ES cell medium containing bFGF (ReproCELL) was replaced. On the 24th, 32nd, and 40th day, the number of total colonies and the number of colonies having morphology of human ES-like cells were counted. As a control, DsRed was used in place of miRNA. The results are shown in FIG. 3. It was found that the number of colonies of induced pluripotent stem cells increased twice or more, as compared to the control, by introduction of three genes in the presence of hsa-miR-372, 373, 302b, 302-367 cluster (including 302b, 302c, 302a, 302d, and 367), 520c, mmu-miR-291a, 294, or 295.

Example 4: Preparation of Induced Pluripotent Stem Cells Through Nuclear Reprogramming of Adult Human Dermal Fibroblasts $3\times10^5$ aHDF-Slc7a1 cells were plated on 60 mm gelatin coated dishes and infected with retrovirus to express DsRed, 4 factors (OCT3/4, SOX2, c-MYC, and KLF4), or 3 factors (OCT3/4, SOX2, KLF4) in the presence of various miRNAs independently. Six days after infection, $5\times10^5$ aHDF-Slc7a1 cells were reseeded on mytomicin-C treated STO cells. Forty days after infection, the number of human ES-like colonies was counted. The same experiment was repeated three times.

Figure 4:
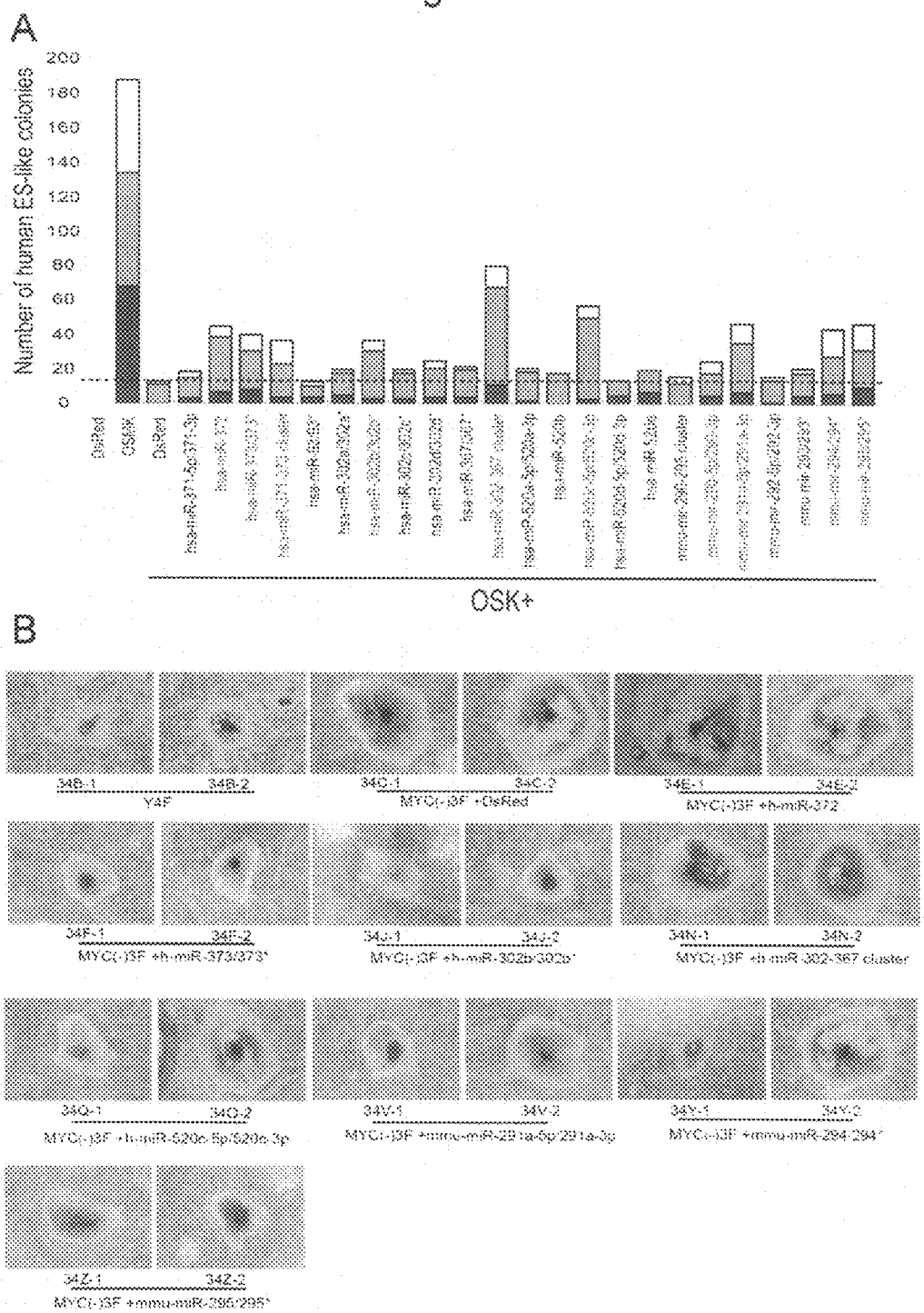
FIGS. 4A-B shows the results of ES-like colonies produced after transduction with 4 factors, i.e., OCT3/4, SOX2, KLF4, and c-MYC(OSMK), as well as with 3 factors, i.e., OCT3/4, SOX2, KLF4 in the presence of various miRNAs (OSK+).

FIG. 4A shows the results of three independent experiments. It was found that the number of colonies of induced pluripotent stem cells increased, as compared to the control, by introduction of three genes in the presence of hsa-miR-372, 373/373* (hsa-miR-373), 371-373 cluster (including 371, 372, and 373), 302b/302b* (hsa-miR-302b), 302-367 cluster (including 302b, 302c, 302a, 302d, and 367), 520c-5p/520c-3p (hsa-miR-520c), mmu-miR-290-5p/290-3p (mmu-miR-290), mmu-miR-291a-5p/291a-3p (mmu-miR-291a), 294/294* (mmu-miR-294), or 295/295* (mmu-miR-295).

FIG. 4B shows the morphology of ES-like colonies of iPS cells by using microscopy.

Example 5: Expression of ES Cell Markers in iPS Cells Produced by Nuclear Reprogramming of Mouse Tail Tip Fibroblasts (TTFs) with 4 Factors (OCT3/4, SOX2, c-MYC, and KLF4) and with 3 Factors (OCT3/4, SOX2, and KLF4)+Mmu-miR-295/295*

$5 \times 10^4$ FbNg TTFs (TTFs derived from Fbx15-β geo/Nanog-IRES-Puro$^r$ reporter mouse) cells were plated on gelatin coated 6-well plates and infected with retrovirus to express 3 factors (Oct3/4, Sox2, Klf4) plus either DsRed (Myc(−)3f+DsRed), mmu-miR-295/295* (Myc(−)3f+mmu-miR-295/295*), or c-Myc (4 factor). On Day 4 after infection, all the cells (Myc(−)3f+DsRed; Myc(−)3f+mmu-miR-295/295*) or 20 times diluted cells (4 factors) were reseeded on Puromycin and Hygromycin-resistant-MSTO (PH-MSTO) cells. Puromycin selection was started on Day 7, 14, 21, 28.

Figure 5:
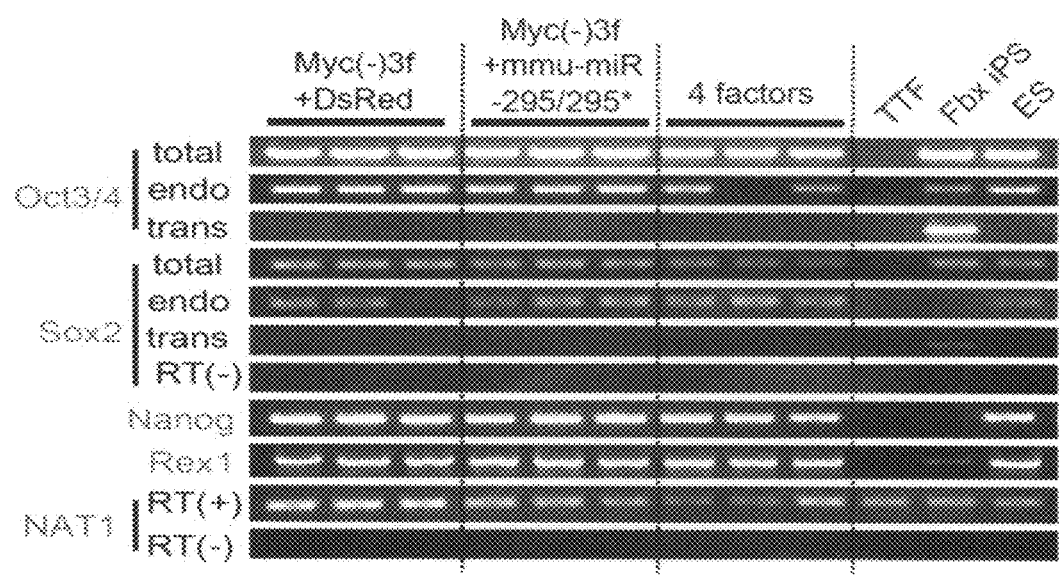
FIG. 5 shows expression of ES cell markers in iPS cells produced by nuclear reprogramming of mouse Tail Tip Fibroblasts (TTFs) with 4 factors (OCT3/4, SOX2, c-MYC, and KLF4) and with 3 factors (OCT3/4, SOX2, and KLF4, i.e. "Myc(−)3f")+mmu-miR-295/295* or DsRed.

RT-PCR analysis using the Rever Tra Ace Kit (Takara) showed that the iPS cells transfected with 4 factors (OCT3/4, SOX2, c-MYC, and KLF4), or with 3 factors (OCT3/4, SOX2, and KLF4)+mmu-miR-295/295* expressed the ES cell specific marker genes Oct3/4, Sox2, Nanog, and that the amounts of expression thereof were equivalent to those obtained with mouse ES cells(ES) and mouse iPS cells (Fbx iPS) (FIG. 5).

Example 6: Preparation of Induced Pluripotent Stem Cells Through Nuclear Reprogramming of Mouse Embryonic Fibroblasts with 3 Factors (OCT3/4, Klf4, and c-Myc) with miRNAs $1 \times 10^5$ Nanog MEFs (MEFs derived from Nanog-MS-Puro$^r$ reporter mouse) were plated on gelatin coated 6-well plates and infected with retrovirus to express 3 factors (Oct3/4, c-MycWT(wild type), and Klf4) with mmu-miR-290-295 cluster, 290-5p/290-3p (mmu-miR-290), 291a-5p/291a-3p (mmu-miR-291), 292-5p/292-3p (mmu-miR-292), 293/293* (mmu-miR-293), 294/294* (mmu-miR-294) or 295/295* (mmu-miR-295) miRNAs (1:1). On day 4 after infection, half of the cells were reseeded on Puromycin and Hygromycin-resistant-MSTO (PH-MSTO) cells. Puromycin selection was started from 14 days after infection.

FIG. 6A shows the number of Nanog GFP positive colonies. The results of three independent experiments are shown with different colors. "DsRed" indicates the combination of Oct3/4, Klf4, c-Myc and DsRed.

FIG. 6B shows the results of RT-PCR analysis. RT-PCR analysis using the Rever Tra Ace Kit (Takara) showed that the iPS cells transfected with 4 factors (OCT3/4, SOX2, c-MYC, and KLF4), or with 3 factors (OCT3/4, SOX2, and KLF4)+mmu-miR-290-295 cluster, 291a-5p/291a-3p, 294/294* and 295/295* expressed the ES cell specific marker genes Oct3/4, Sox2, Nanog, and that the amounts of expression thereof were equivalent to those obtained with mouse ES cells (ES) and mouse iPS cells (Fbx iPS).

Example 7: iPS Induction with Fb-Ng MEFs (MEFs Derived from Fbx15-β Geo/Nanog-IRES-Puro$^r$ Reporter Mouse) Over-Expressing Oct3/4, c-Myc, and Klf4 ("Sox(−)")+Mmu-miR-295/295* or Hsa-miR-302-367 Cluster miRNAs $1 \times 10^5$ Fb-Ng MEFs (MEFs derived from Fbx15-β geo/Nanog-IRES-Puro$^r$ reporter mouse) were plated on gelatin coated 6-well plates and infected with retrovirus to express 3 factors (Oct3/4, c-MycWT(wild type), Klf4)+miR-295/295* or hsa-miR-302-367 cluster. On day 4 after infection, cells were reseeded on Puromycin and Hygromycin resistant mytomycin-C treated STO cells (PH-MSTO) by in 6-well or 10 cm dishes. Puromycin selection was started from 7 days after infection.

FIG. 7A shows cell morphology of MEFs transduced with Oct3/4, c-Myc, and Klf4 ("Sox(−)")+mmu-miR-295/295*. The colonies showed morphology similar to that of ES cells. FIG. 7B shows chimeras derived from iPS cells induced with Sox(−)3f+mmu-miR-295/295*.

FIG. 7C shows embryoid body (EB)-mediated in vitro differentiation by human iPS cells. Human iPS cells (61B1, 61N2) which were established by transduction of 4 genes (OCT3/4, KLF4, SOX2, and c-MYC, i.e. "OSMK") or 3 genes (OCT3/4, KLF4, and c-MYC, i.e., "OMK(SOX(−)")+hsa-miR-302-367 cluster miRNA were plated on a low-binding dish, and embryoid bodies were formed on 100 mm dishes in accordance with the method described in Takahashi et al., *Cell* 131:861-872, 2007. After culturing for 2 weeks, the cells were stained using an antibody against each of α-fetoprotein (R&D systems) which is a differentiation marker for endodermal cells, α-smooth muscle actin (DAKO) which is a differentiation marker for mesodermal cells, and Glial Fibrillary Astrocytic Protein (GFAP) (DAKO) which is a differentiation marker for ectodermal cells. The expression of each marker was confirmed by staining. Nuclei were stained with Hoechst 33342 (Invitrogen).

Example 8: iPS Induction with 4 Factors (OCT3/4, SOX2, MYC, KLF4) or 3 Factors (OCT3/4, MYC, KLF4, i.e., "SOX(−)3") with and without Various miRNAs $3 \times 10^5$ cells of aHDF-Slc7a1 cells were plated on 60 mm gelatin coated dishes and infected with retrovirus to express 4 factors: OCT3/4, SOX2, c-MYC, KLF4 (OSMK) or 3 factors: SOX(−)$_3$ factors (OMK) in the presence of miRNAs as indicated (OMK:mock or miRNAs=2.5:1.5), or with 2 factors: OCT3/4+KLF4 (OK) in the presence of miRNAs as indicated. Cells were infected with DsRed as control. Six days after infection, $5 \times 10^5$ aHDF-Slc7a1 cells were reseeded on mytomicin-C treated STO cells (MSTOcells). On Day 40 after infection, the number of ES-like colonies was counted.

TABLE 3 shows the number of human ES(hES)-like colonies in aHDF-Slc7a1 cells tranduced with OSMK, OMK with or without miRNAs, and with OK with or without miRNAs. The hES-like colonies showed in cells transduced with OSMK, OMK+miRNAs (hsa-miR-371-373 cluster, hsa-miR-302-367 cluster, or hsa-miR-371-373 cluster+302-367 cluster) were detected by six independent experiments (Exp. 54, 61, 63, 114, 130, and 133).

TABLE 3

| | | Number of hES-like colonies | | Exp. 54 | Exp. 61 | Exp. 63 | Exp. 114 | Exp. 130 | Exp. 133 |
|---|---|---|---|---|---|---|---|---|---|
| A | control | DsRed | | 0 | 0 | 0 | 0 | 0 | 0 |
| B | OSMK | Y4f (O:S:M:K = 1:1:1:1) | | 5 | 41 | 54 | 37 | 39 | 100 |

TABLE 3-continued

| | | Number of hES-like colonies | Exp. 54 | Exp. 61 | Exp. 63 | Exp. 114 | Exp. 130 | Exp. 133 |
|---|---|---|---|---|---|---|---|---|
| G | | Y4f (OMK:S = 2.5:1.5) | | | 13 | 7 | 4 | 22 |
| H | OMK + mock | Sox(−)Y3f + mock | 0 | 0 | 0 | 0 | 0 | 0 |
| I | or miRNA | Sox(−)Y3f + h-miR-371-373 cluster | 0 | 0 | 1 | 0 | 0 | 0 |
| J | | Sox(−)Y3f + h-miR-302-367 cluster | 0 | 2 | 3 | 0 | 8 | 5 |
| K | | Sox(−)Y3f + h-mir-371-373 cluster + 302-367 cluster | | | | 0 | 0 | 6 |
| M | OK + mock | OK + mock | | | | 0 | 0 | 0 |
| N | or miRNA | OK + h-miR-371-373 cluster | | | | 0 | 0 | 0 |
| O | | OK + h-miR-302-367 cluster | | | | 0 | 0 | 4 |
| P | | OK + h-miR-371-373 cluster + 302-367 cluster | | | | 1 | 0 | 0 |

FIG. 8A shows cell morphology of iPS cells induced with OSMK (61B1); OMK (SOX(−))+hsa-miR-302-367 cluster miRNA (61N2); and OK+hsa-miR-302-367 cluster miRNA (133O1). FIG. 8B shows that iPS cells induced with OK+hsa-miR-302-367 cluster miRNA (133O1) is positive for alkaline phosphatase.

Moreover, the present inventors have confirmed that the combination of OCT3/4 and NANOG can induce iPS cells (or hES-like cells) from somatic cells (U.S. Provisional Application No. 61/193,122, filed Oct. 30, 2008).

Example 9: Confirmation of Differentiation Pluripotency of iPS Cells

Figure 9:
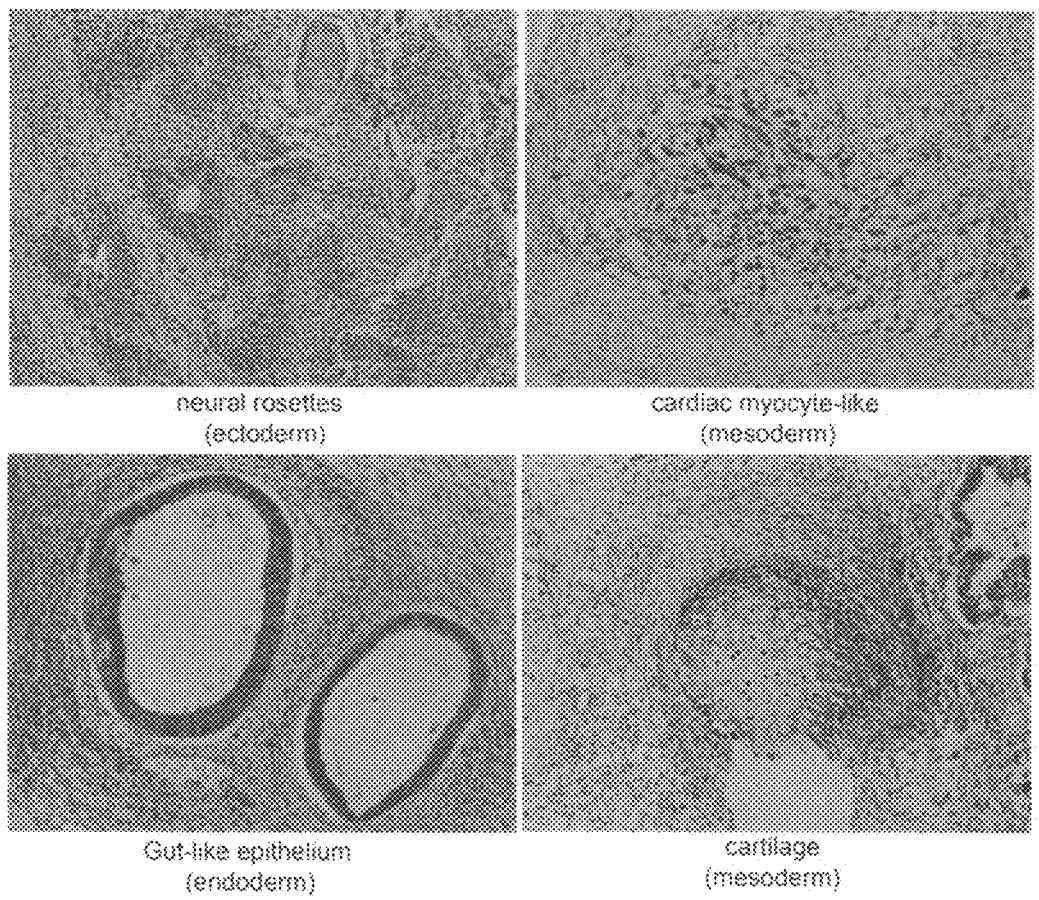
FIG. 9 shows formation of teratoma in a SCID mouse with inoculated human iPS cells, which cells were obtained by introducing OCT3/4 gene, KLF4 gene, c-MYC gene, and hsa-miR-302-367 cluster into human adult fibroblast cells (aHDF). Specifically, into the aHDF-Slc7a1 cells, which are capable of expressing the mouse ecotropic receptor Slc7a1 by transduction via rentivirus, were introduced OCT3/4 gene, KLF4 gene, c-MYC gene and hsa-miR-302-367 cluster via retroviral vector, thereby generating human iPS cells, which were subsequently used for inoculating them to a mouse. Following the inoculation, the formed teratoma was removed and sectioned, then stained with hematoxylin and eosin for observation of the stained cells.

Human iPS cells (61N2), which was obtained by introducing a combination of OCT3/4, KLF4 and c-MYC (i.e., SOX(−)3F) with hsa-miR-302-367 cluster into the human cell line aHDF-Slc7a1 cells, were intradermally inoculated into the lateral abdomen of the back of a SCID mouse. Nine weeks after inoculation, teratoma was removed, fixed, embetted in paraffin, and stained with hematoxylin and eosin. The histological observation showed that the teratoma contained a variety of tissues including neural rosettes (ectoderm), cardiac myocyte-like structure (mesoderm), gut-like epithelium (endoderm), and cartilage (mesoderm), thus confirming that the iPS cells (61N2) can differentiate into three embryonic germ layers and have pluripotency (FIG. 9).

Example 10: Induction of iPS Cells with a Single Gene (OCT3/4) in the Presence of miRNA (1) Colony Formation and ALP Staining The human cell line aHDF-Slc71 cells were seeded on 6-well plate at $1\times10^5$ cells per well. On the next day, to the cells were introduced any of the following gene or gene combinations through retroviral vector:
1. GFP gene (a negative control).
2. OCT3/4 gene, SOX2 gene, c-MYC gene, and KLF4 gene (1:1:1:1).
3. OCT3/4 gene, SOX2 gene, and KLF4 gene (1:1:1).
4, OCT3/4 gene, KLF4 gene, and mock gene (pMSx empty vector) (1:1:1).
5. OCT3/4 gene, KLF4 gene, and hsa-miR-302-367 cluster (1:1:1).
6. OCT3/4 gene and mock gene (1:1).
7. OCT3/4 gene and hsa-miR-302-367 cluster (1:1).
8. KLF4 gene and mock gene (1:1).
9. KLF4 gene and hsa-miR-302-367 cluster (1:1).
10. hsa-miR-302-367 cluster.

Figure 10:
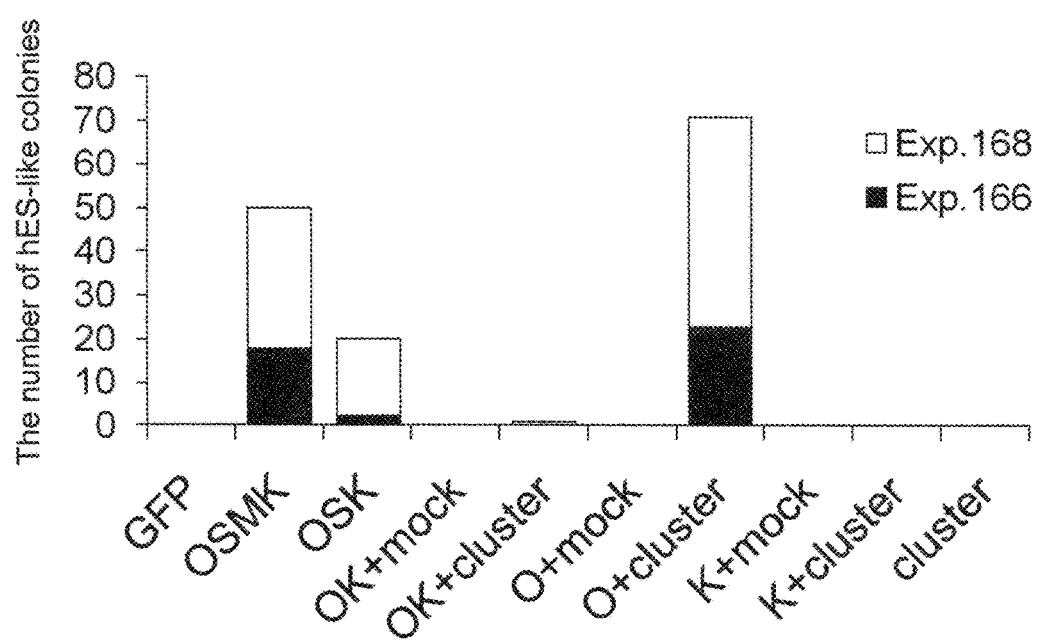
FIG. 10 shows the results obtained when human adult dermal fibroblast cells (aHDF-Slc7a1) were tried to be reprogrammed with a combination of OCT3/4 gene, KLF4 gene, or OCT3/4+KLF4 genes, and hsa-miR-302-367 cluster miRNA.

On day 6 after infection, the cells were detached, $5\times10^5$ cells of which were reseeded onto MSTO feeder cells. Thereafter, at one day intervals, human ES cell medium containing bFGF (ReproCELL) was replaced, and on day 40 after infection, the number of colonies with ES cell-like morphology was counted. Results of independent duplicate experiments are shown in TABLE 4 and in FIG. 10, which shows graphed results of TABLE 4.

TABLE 4

| The number of hES-like colonies | Exp. 166 | Exp. 168 |
|---|---|---|
| GFP | 0 | 0 |
| OSMK | 18 | 32 |
| OSK | 2 | 18 |
| OK + mock | 0 | 0 |
| OK + cluster | 0 | 1 |
| O + mock | 0 | 0 |
| O + cluster | 23 | 48 |
| K + mock | 0 | 0 |
| K + cluster | 0 | 0 |
| cluster | 0 | 0 |

When OCT3/4 gene was introduced into aHDF-Slc7a1 cells in the presence of hsa-miR-302-367 cluster, iPS cell colonies having ES cell-like morphology were obtained. In this case the colony counts were greater than in the case that four genes (i.e., OCT3/4 gene, SOX2 gene, c-MYC gene, and KLF4 gene) were introduced. Thus, according to the present invention, it was demonstrated for the first time that iPS cells could be established even with use of a single gene OCT3/4 in the presence of miRNA(s).

Figure 11:
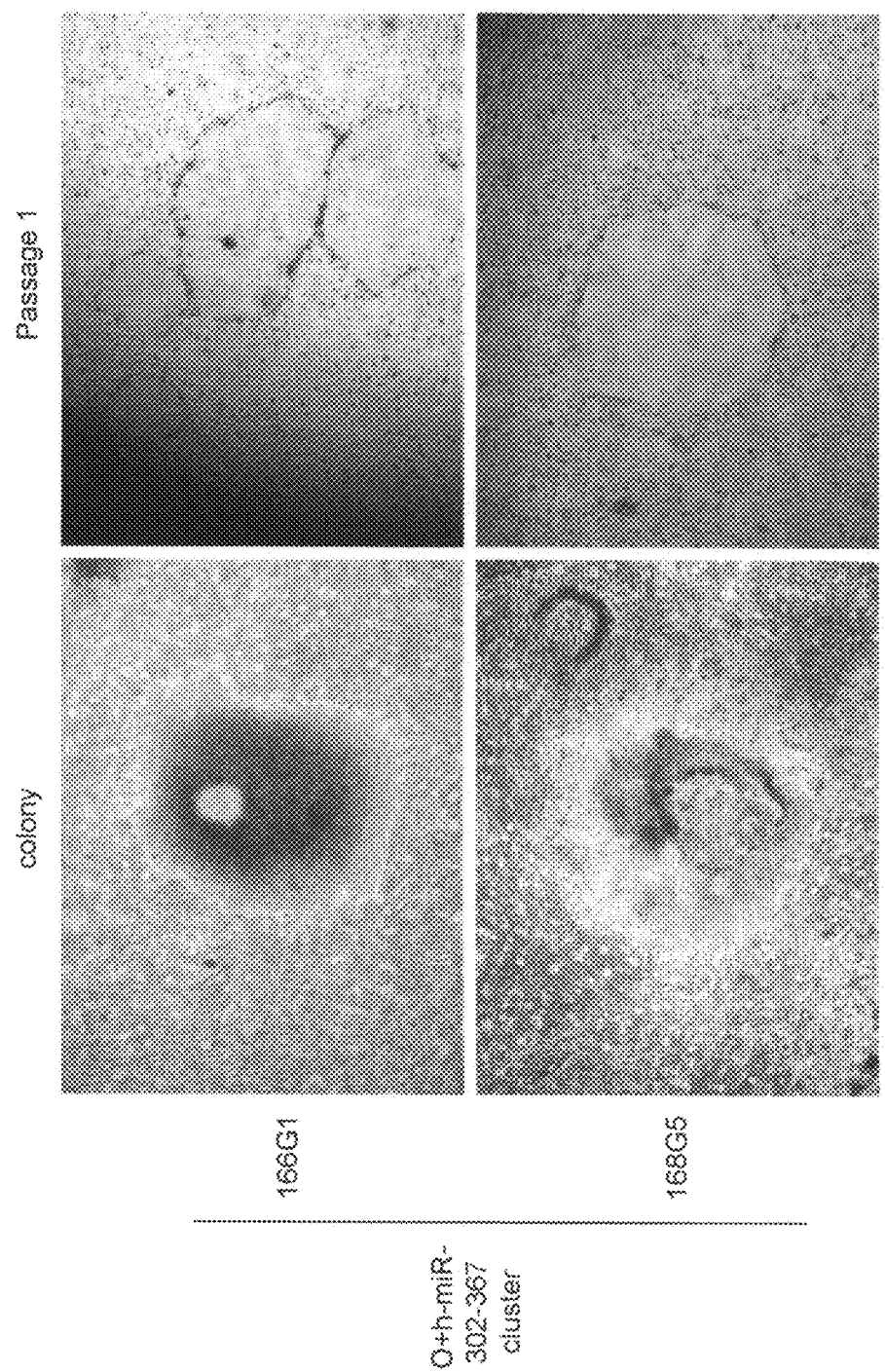
FIG. 11 shows colony images, at the colony formation and at the first passage, of the iPS cells, i.e. 166G1 and 168G5, which were established by introduction of the combination of OCT3/4 gene and hsa-miR-302-367 cluster miRNA.
Figure 12:
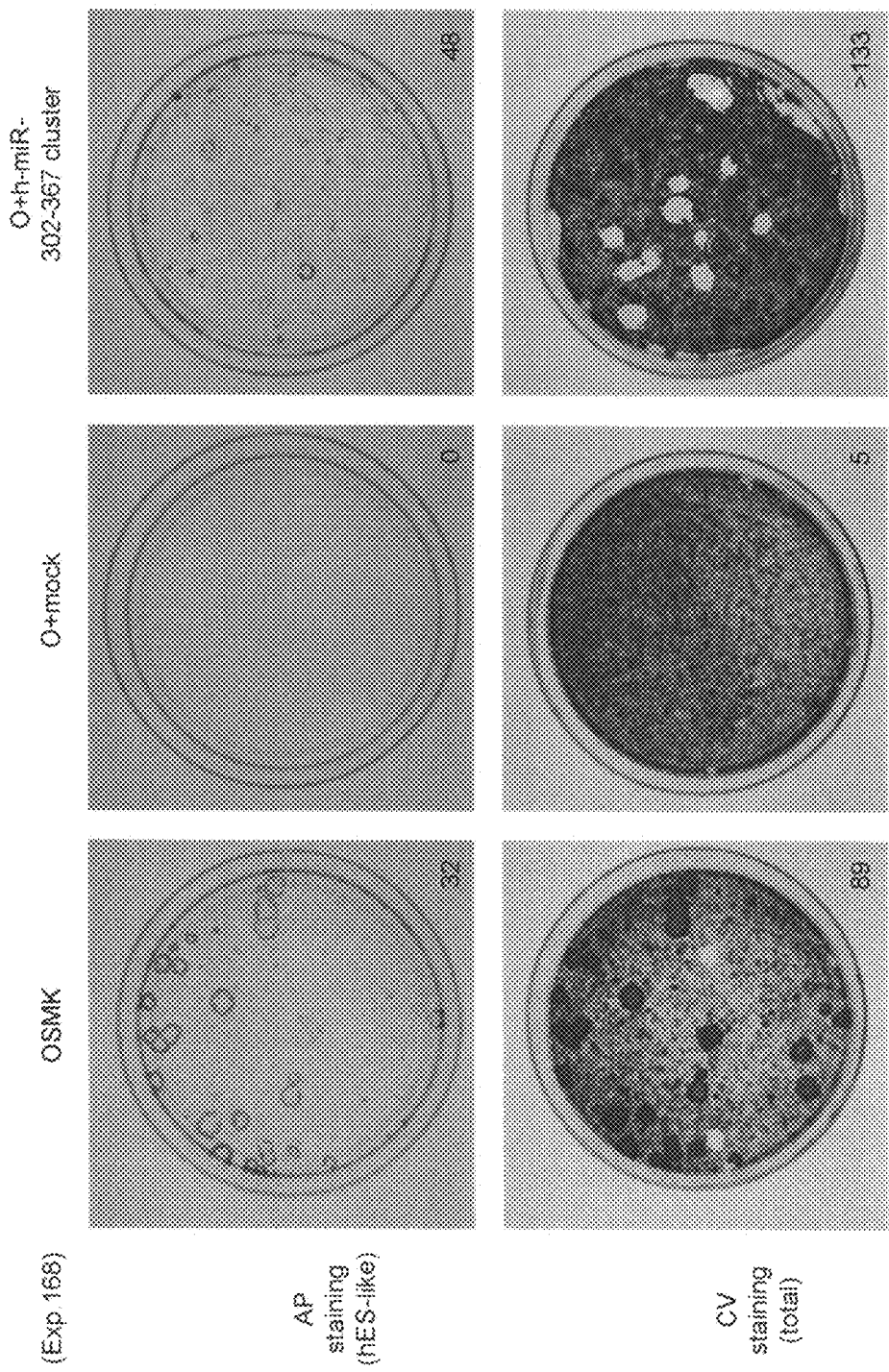
FIG. 12 shows that iPS cells, Exp. 168, established by introduction of OCT3/4 gene+hsa-miR-302-367 cluster miRNA are positive for alkaline phosphatise (AP) (top panels), and also shows the results of Crystal Violet (CV) staining (bottom panels). This figure further shows the respective results of AP staining and CV staining for iPS cells, which were induced with OSMK or O+mock in Exp. 168 of Example 10, as a positive control or a negative control, respectively.
Figure 13:
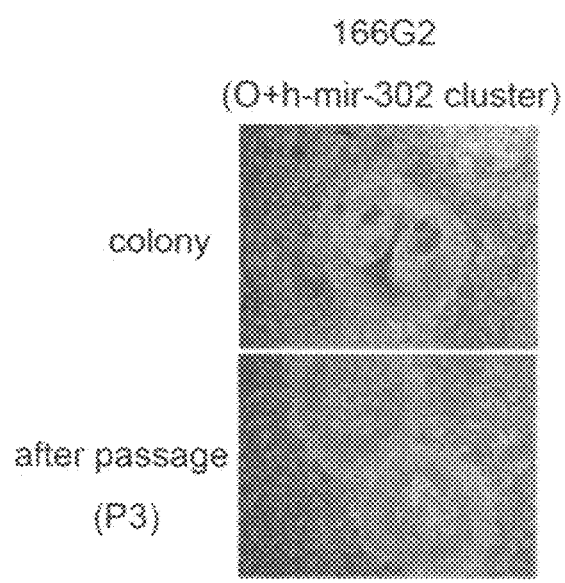
FIG. 13 shows photographs of iPS cell clones (166G2) established by introducing OCT3/4 and hsa-mir-302-367 cluster miRNA.

For the iPS cells, i.e. 166G1 and 168G5, which were established by introduction of the combination of OCT3/4 gene and hsa-miR-302-367 cluster miRNA, colony images at the colony formation and at the first passage are shown in FIG. 11. Also, in FIG. 12, there are provided results showing that the iPS cells were positive for alkaline phosphatase, thus in an undifferentiated form. For another iPS cell clone, i.e. 166G2, colony images at colony formation and at the 3rd passage are shown in FIG. 13.

(2) Genomic-PCR Analysis

Figure 14:
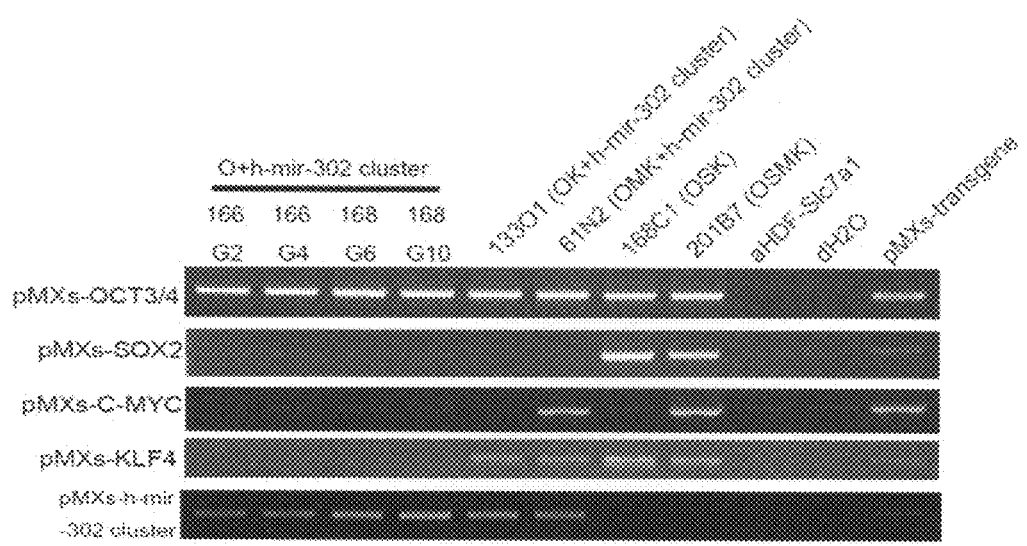
FIG. 14 shows photographs demonstrating the results of genomic-PCR analysis.

Genomic-PCR analysis was performed as described previously in Cell, 131, 861-872 (2007). As a result, the introduced OCT3/4 gene and hsa-miR-302-367 cluster miRNA gene were integrated into genome of any iPS cell clones (166G2, 166G4, 168G6, 168G10) (FIG. 14). On the contrary, the genes which have not been introduced into aHDF-Slc7a1 were not detected in any iPS cell clones (FIG. 14).

(3) RT-PCR Analysis

Figure 15:
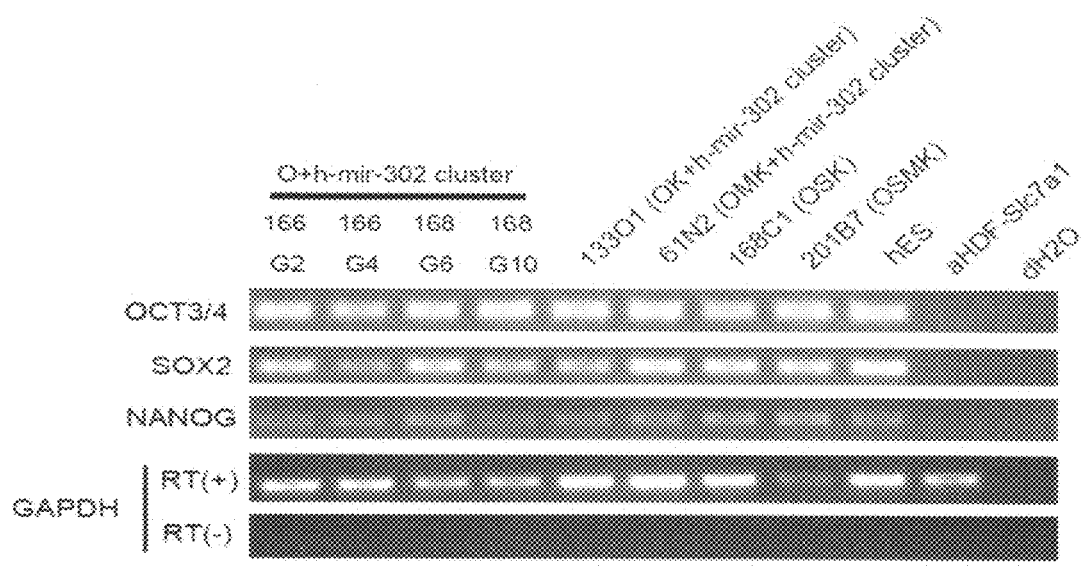
FIG. 15 shows photographs demonstrating the results of RT-PCR analysis.

RT-PCR analysis was performed using Rever Tra Ace kit(Takara). As a result, all iPS cell clones (166G2, 166G4, 168G6, 168G10) expressed the human ES cell specific marker genes OCT3/4, SOX2 and NANOG, and expression levels of the marker genes were substantially equivalent to those of human ES cells or iPS cells established in the past (201B7) (FIG. 15). From these results, we identified the cells established by introducing OCT3/4 and miRNA, as iPS cells.

(4) In Vitro Differenciation

Figure 16:
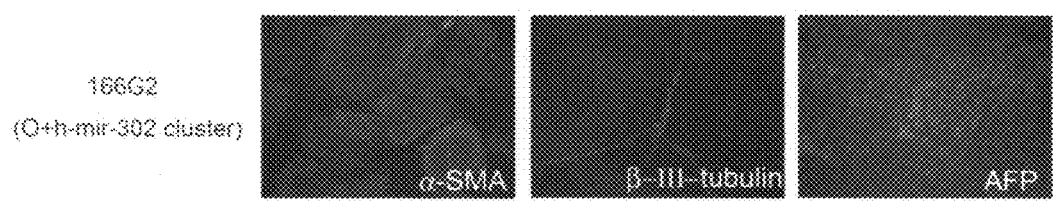
FIG. 16 shows photographs demonstrating the expression of mesoderm-(α-SMA), ectoderm-(βIII-tubulin), and endoderm-(AFP) differentiation markers in the iPS clones.

The present inventors confirmed whether the established iPS cells were pluripotent by in vitro differentiation. To form embryoid bodies, the cells were harvested and transferred to poly-hydroxyethyl methacrylate (HEMA)-coated dishes and incubated for 8 days. After floating culture, the embryoid bodies formed were plated onto gelatin-coated plates and incubated for additional 8 days. After incubation, the cells were fixed with 4% paraformaldehyde, permeabilized, and blocked with PBS containing 5% normal goat serum, 1% BSA and 0.2% TritonX-100. The expression of differentiation markers (βIII-tublin, α-SMA, AFP) was examined by immunocytochemistry. As primary antibodies, anti-βIII-tublin (1:100, Chemicon), anti-α-smooth muscle actin (α-SMA) (1:500, DAKO) and anti-α-fetoprotein (AFP) (1:100, R&D systems) were used. Cy3-labeled anti-mouse IgG (1:500, Chemicon) was used as secondary antibody. Nuclei were stained with Hoechst 33342 (Invitrogen). The results are shown in FIG. 16. Eight days after floating culture, the iPS cells formed embryoid bodies. After incubation on the gelatin-coated plates, the cells changed morphologically to various cell types. Immunocytochemistry showed that the iPS cells differentiated into three germ layers such as ectoderm (βIII-tublin), mesoderm (α-SMA) and endoderm (AFP)(FIG. 16).

INDUSTRIAL APPLICABILITY

The present invention provides an efficient method for preparing induced pluripotent stem cells. The method of the present invention has higher nuclear reprogramming efficiency as compared to conventional methods. For example, safe induced pluripotent stem cells can be efficiently produced without using c-Myc or gene products thereof. Accordingly, the method of the present invention enables efficient production of highly safe induced pluripotent stem cells from a patient's own somatic cells. Cells differentiated from such pluripotent stem cells (for example, myocardial cells, insulin-producing cells, or nerve cells) can be safely utilized in stem cell transplantation therapies for treatment of various diseases, such as heart failure, insulin dependent diabetes mellitus, Parkinson's diseases, and spinal cord injury.

Although the present invention has been described in considerable detail with regard to certain versions thereof, other versions are possible, and alterations, permutations, and equivalents of the versions shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All the disclosures of the above-described patents, patent applications and publications are incorporated herein by reference in their entirety.

The attached Sequence Listing includes SEQ ID NOs: 13 and 14, as well as those sequences disclosed in PCT/JP2008/59586, which is incorporated by reference herein in its entirety.

What is claimed is:

1. A method of preparing an induced pluripotent stem cell from a mammalian somatic cell, comprising nuclear reprogramming the mammalian somatic cell under culture conditions which allow for mammalian somatic cell reprogramming to pluripotency with at least one miRNA and an expression vector encoding at least one nuclear reprogramming factor, wherein the at least one miRNA increases efficiency of the nuclear reprogramming of the mammalian somatic cell compared to nuclear reprogramming of the mammalian somatic cell with the expression vector in the absence of the at least one miRNA, wherein the at least one miRNA is one or two or more miRNAs contained in one or two or more RNAs selected from the group consisting of: hsa-miR-372; hsa-miR-373 or hsa-miR-373/373*; hsa-miR-371-373 cluster; hsa-miR-302b or hsa-miR-302b/302b*; hsa-miR-302-367 cluster; hsa-miR-520c or hsa-miR-520c-5p/520c-3p; mmu-miR-291a or mmu-miR-291a-5p/291a-3p; mmu-miR-294 or mmu-miR-294/294*; and mmu-miR-295 or mmu-miR-295/295*, and wherein the at least one nuclear reprogramming factor comprises at least (i) an Oct3/4 gene, (ii) an Oct3/4 gene and a Klf4 gene, (iii) an Oct3/4 gene and a Nanog gene, or (iv) an Oct3/4 gene, Klf4 gene, and a Myc family gene, but it does not comprise a Sox family gene.

2. A method of increasing the efficiency of nuclear reprogramming for inducing an induced pluripotent stem cell from a mammalian somatic cell, comprising subjecting the mammalian somatic cell to nuclear reprogramming with an expression vector encoding at least one nuclear reprogramming factor in the presence of at least one miRNA under culture conditions which allow for mammalian somatic cell reprogramming to pluripotency, wherein the at least one miRNA increases efficiency of the nuclear reprogramming of the mammalian somatic cell compared to nuclear reprogramming of the somatic cell with the expression vector in the absence of the at least one miRNA, wherein the at least one miRNA is one or two or more miRNAs contained in one or two or more RNAs selected from the group consisting of: hsa-miR-372; hsa-miR-373 or hsa-miR-373/373*; hsa-miR-371-373 cluster; hsa-miR-302b or hsa-miR-302b/302b*; hsa-miR-302-367 cluster; hsa-miR-520c or hsa-miR-520c-5p/520c-3p; mmu-miR-291a or mmu-miR-291a-5p/291a-3p; mmu-miR-294 or mmu-miR-294/294*; and mmu-miR-295 or mmu-miR-295/295*, and wherein the at least one nuclear reprogramming factor comprises at least (i) an Oct3/4 gene, (ii) an Oct3/4 gene and a Klf4 gene, (iii) an Oct3/4 gene and a Nanog gene, or (iv) an Oct3/4 gene, a Klf4 gene, and a Myc family gene, but it does not comprise a Sox family gene.

3. The method according to claim 1 or 2, wherein the at least one miRNA is expressed in embryonic stem cells at a higher level than in somatic cells.

4. The method according to claim 1 or 2, wherein the Myc family gene is a c-Myc gene.

5. The method according to claim 1 or 2, wherein the at least one nuclear reprogramming factor is an Oct3/4 gene.

6. The method according to claim 1 or 2, wherein the at least one miRNA is introduced into the mammalian somatic cell in the form of a vector comprising DNA encoding the miRNA or a precursor RNA thereof.

7. The method according to claim 1 or 2, wherein the at least one miRNA is one or two or more miRNAs contained in one or two or more RNAs selected from the group consisting of RNAs represented by SEQ ID NOS:1 to 5, 10 to 12, and 14.

8. The method according to claim 1 or 2, wherein the at least one miRNA is 18-25 nucleotides in length.

9. The method according to claim 1 or 2, wherein the mammalian somatic cell is a human somatic cell.

* * * * *